(12) United States Patent
Suh et al.

(10) Patent No.: US 11,026,801 B2
(45) Date of Patent: *Jun. 8, 2021

(54) MODULAR PLATE AND CAGE ELEMENTS AND RELATED METHODS

(71) Applicant: CTL Medical Corporation, Addison, TX (US)

(72) Inventors: Jon Suh, Ambler, PA (US); Sean Suh, Milltown, NJ (US)

(73) Assignee: CTL Medical Corporation, Addison, TX (US)

( * ) Notice: Subject to any disclaimer, the term of this patent is extended or adjusted under 35 U.S.C. 154(b) by 121 days.

This patent is subject to a terminal disclaimer.

(21) Appl. No.: 16/291,278

(22) Filed: Mar. 4, 2019

(65) Prior Publication Data
US 2019/0192309 A1   Jun. 27, 2019

Related U.S. Application Data

(63) Continuation of application No. 15/244,868, filed on Aug. 23, 2016, now Pat. No. 10,219,912.

(60) Provisional application No. 62/270,141, filed on Dec. 21, 2015.

(51) Int. Cl.
*A61F 2/44* (2006.01)
*A61F 2/30* (2006.01)

(52) U.S. Cl.
CPC ............ *A61F 2/4455* (2013.01); *A61F 2/447* (2013.01); *A61F 2002/3008* (2013.01); *A61F 2002/30014* (2013.01); *A61F 2002/30092* (2013.01); *A61F 2002/3093* (2013.01); *A61F 2002/30383* (2013.01); *A61F 2002/30448* (2013.01); *A61F 2002/30471* (2013.01); *A61F 2002/30538* (2013.01); *A61F 2002/30578* (2013.01); *A61F 2002/30593* (2013.01); *A61F 2002/30604* (2013.01); *A61F 2002/30616* (2013.01); *A61F 2002/30785* (2013.01); *A61F 2002/30787* (2013.01); *A61F 2002/30841* (2013.01); *A61F 2002/30881* (2013.01); *A61F 2002/30904* (2013.01); *A61F 2220/0016* (2013.01)

(58) Field of Classification Search
CPC ...... A61F 2/4455; A61F 2/446; A61F 2/4465; A61F 2/447
See application file for complete search history.

(56) References Cited

U.S. PATENT DOCUMENTS

2013/0110238 A1\*   5/2013   Lindemann ........... A61F 2/4465
                                                          623/17.12

\* cited by examiner

*Primary Examiner* — Andrew Yang
(74) *Attorney, Agent, or Firm* — Brainspark Associates, LLC

(57) ABSTRACT

An interbody system for implanting between vertebrae, the interbody system comprises a cage having a cage body that includes a graft chamber having a volume that receives graft material, a sagittal wall that forms a portion of the graft chamber, and a wall membrane that forms another portion of the graft chamber. The interbody system may comprise an interbody device that includes an aperture that receives a bone fastener, wherein the wall membrane interacts with the bone fastener. The wall membrane may bend as result of a force applied by the bone fastener to a portion of the wall membrane, thereby providing directional support to the bone fastener and/or forcing graft material from the graft chamber.

19 Claims, 20 Drawing Sheets

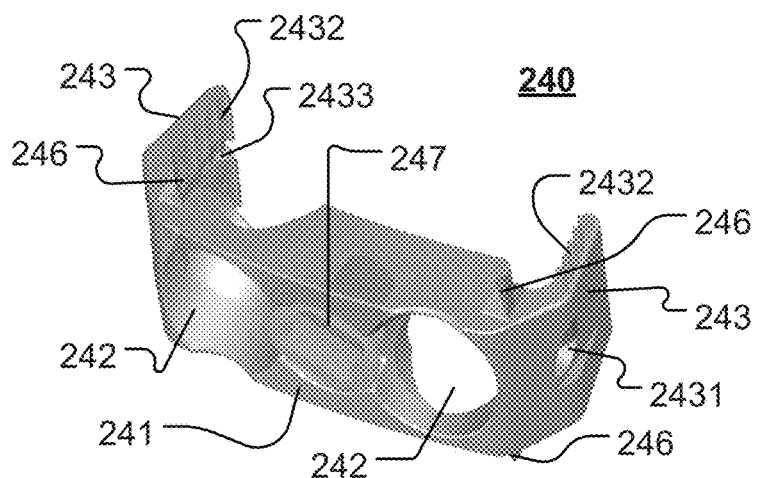
FIG. 13A
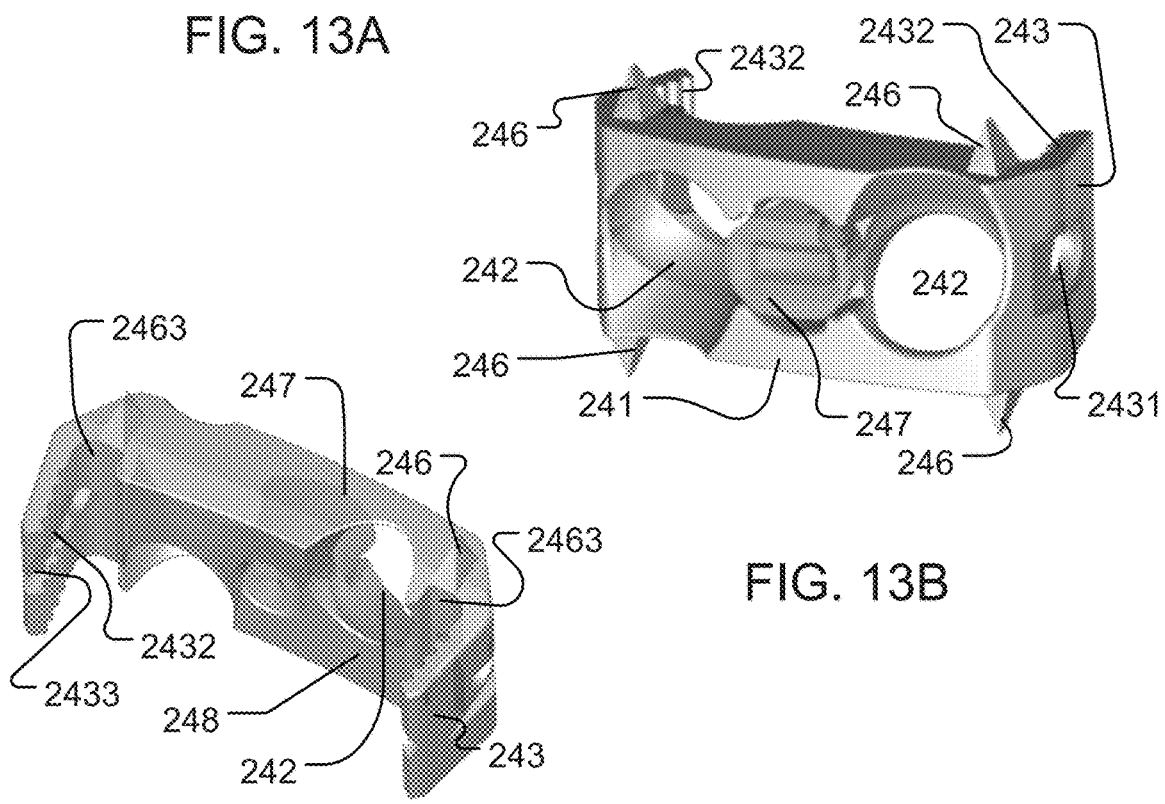
FIG. 13B
FIG. 13C

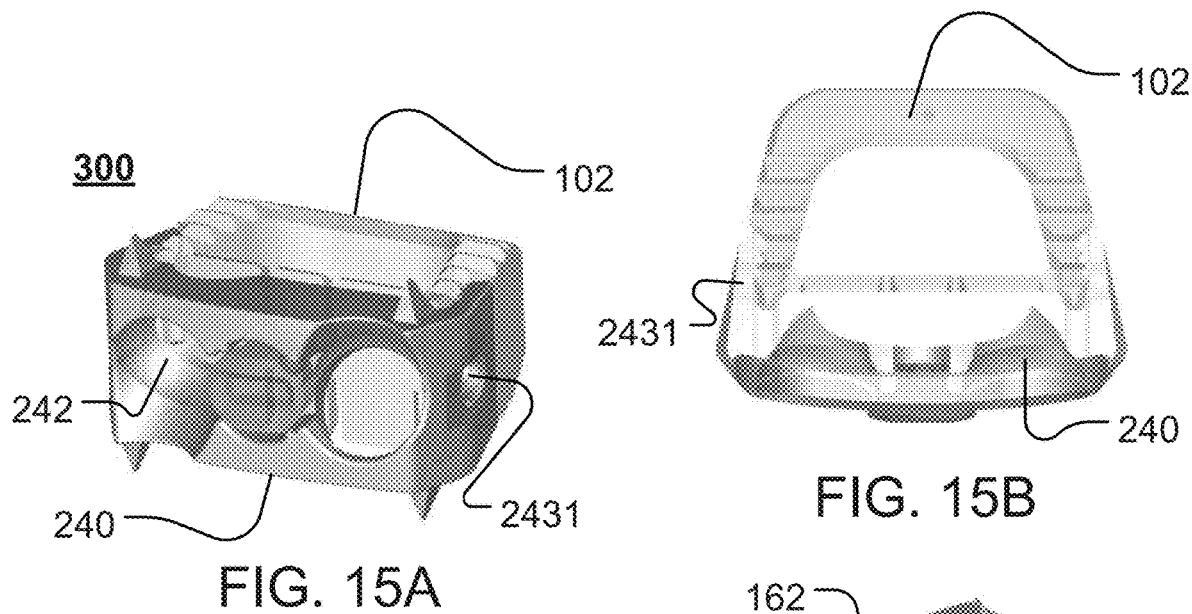
FIG. 15A
FIG. 15B
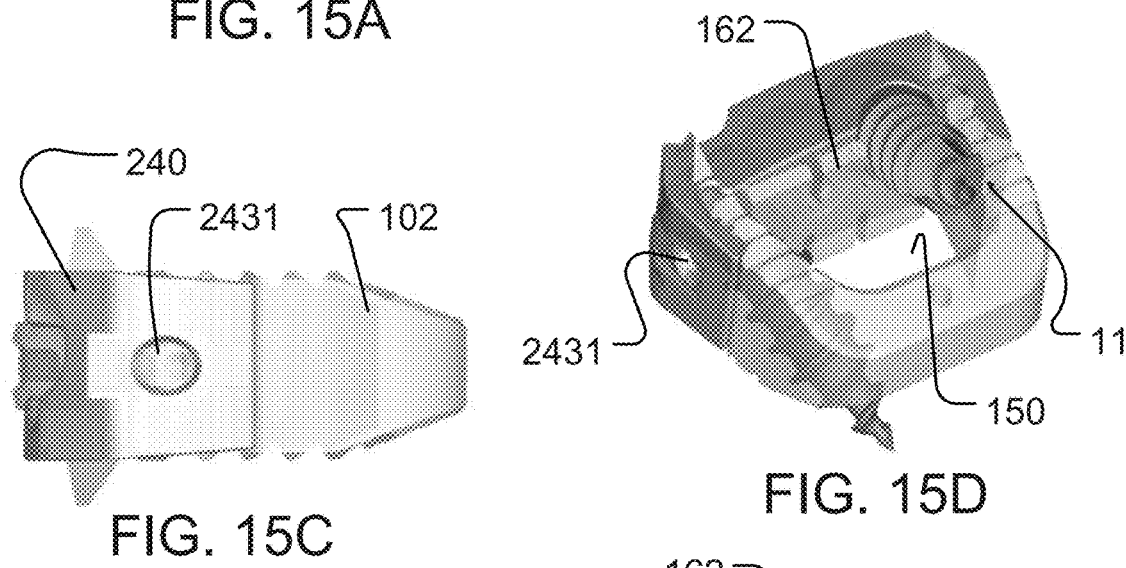
FIG. 15C
FIG. 15D
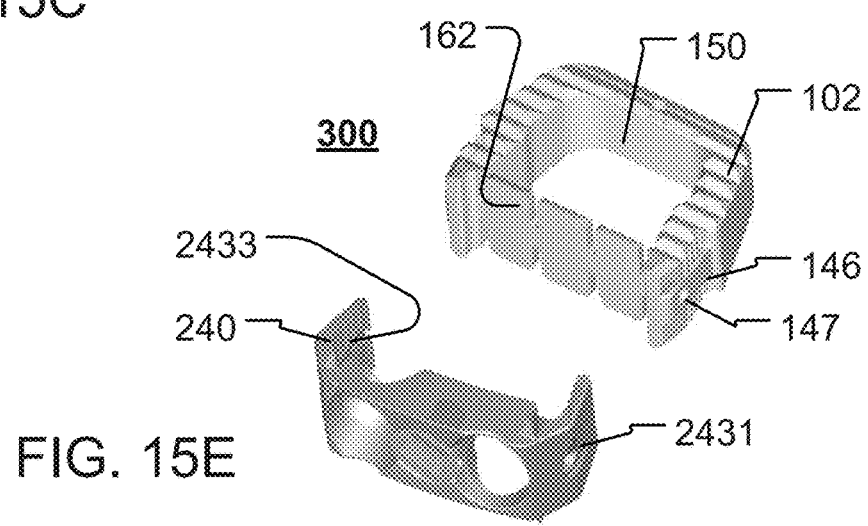
FIG. 15E

MODULAR PLATE AND CAGE ELEMENTS AND RELATED METHODS

CROSS-REFERENCE TO RELATED APPLICATIONS

This application is a continuation of U.S. patent application Ser. No. 15/244,868, filed Aug. 23, 2016 and entitled "MODULAR PLATE AND CAGE ELEMENTS AND RELATED METHODS," which claims priority to and benefit thereof from U.S. Provisional Patent Application No. 62/270,141, filed Dec. 21, 2015, titled "MODULAR PLATE AND CAGE ELEMENTS AND RELATED METHODS," the disclosures of which are both hereby incorporated herein by reference in their entireties.

FIELD OF THE DISCLOSURE

The present disclosure relates to intervertebral and intradiscal implants and related systems and methods. More specifically, the present disclosure relates to intervertebral and intradiscal devices, systems, and methods for deployment within a body of a patient.

BACKGROUND OF THE DISCLOSURE

In mammals, the spinal (or vertebral) column is one of the most important parts. The spinal column provides the main support necessary for mammals to stand, bend, and twist.

In humans, the spinal column is generally formed by individual interlocking vertebrae, which are classified into five segments, including (from head to tail) a cervical segment (vertebrae C1-C7), a thoracic segment (vertebrae T1-T12), a lumbar segment (vertebrae L1-L5), a sacrum segment (vertebrae S1-S5), and coccyx segment (vertebrate Co1-Co5). The cervical segment forms the neck, supports the head and neck, and allows for nodding, shaking and other movements of the head. The thoracic segment attaches to ribs to form the ribcage. The lumbar segment carries most of the weight of the upper body and provides a stable center of gravity during movement. The sacrum and coccyx make up the back walls of the pelvis.

Intervertebral discs are located between each of the movable vertebra. Each intervertebral disc typically includes a thick outer layer called the disc annulus, which includes a crisscrossing fibrous structure, and a disc nucleus, which is a soft structure located at the center of the disc. The intervertebral discs function to absorb force and allow for pivotal movement of adjacent vertebra with respect to each other.

In the vertebral column, the vertebrae increase in size as they progress from the cervical segment to the sacrum segment, becoming smaller in the coccyx. At maturity, the five sacral vertebrae typically fuse into one large bone, the sacrum, with no intervertebral discs. The last three to five coccygeal vertebrae (typically four) form the coccyx (or tailbone). Like the sacrum, the coccyx does not have any in vertebral discs.

Each vertebra is an irregular bone that varies in size according to its placement in the spinal column, spinal loading, posture and pathology. While the basic configuration of vertebrae varies, every vertebra has a body that consists of a large anterior middle portion called the centrum and a posterior vertebral arch called the neural arch. The upper and lower surfaces of the vertebra body give attachment to into vertebral discs. The posterior part of a vertebra forms a vertebral arch that typically consists of two pedicles, two laminae, and seven processes. The laminae give attachment to the ligament flava, and the pedicles have a shape that forms vertebral notches to form the intervertebral foramina when the vertebrae articulate. The foramina are the entry and exit passageways for spinal nerves. The body of the vertebra and the vertical arch form the vertebral foramen, which is a large, central opening that accommodates the spinal canal that encloses and protects the spinal cord.

The body of each vertebra is composed of cancellous bone that is covered by a coating of cortical bone. The cancellous bone is a spongy type of osseous tissue, and the cortical bone is a hard and dense type of osseous tissue. The vertebral arch and processes have thicker coverings of cortical bone.

The upper and lower surfaces of the vertebra body are flattened and rough. These surfaces are the vertebral endplates that are in direct contact with the intervertebral discs. The endplates are formed from a thickened layer of cancellous bone, with the top layer being denser. The endplates contain adjacent discs and evenly spread applied loads. The endplates also provide anchorage for the collagen fibers of the disc.

FIG. 1 shows a portion of a patient's spinal column 2, including vertebra 4 and intervertebral discs 6. As noted earlier, each disc 6 forms a fibrocartilaginous joint between adjacent vertebrae 4 so as to allow relative movement between adjacent vertebrae 4. Beyond enabling relative motion between adjacent vertebrae 4, each disc 6 acts as a shock absorber for the spinal column 2.

As noted earlier, each disc 6 comprises a fibrous exterior surrounding an inner gel-like center which cooperate to distribute pressure evenly across each disc 6, thereby preventing the development of stress concentrations that might otherwise damage and/or impair vertebrae 4 of spinal column 2. Discs 6 are, however, subject to various injuries and/or disorders which may interfere with a disc's ability to adequately distribute pressure and protect vertebrae 4. For example, disc herniation, degeneration, and infection of discs 6 may result in insufficient disc thickness and/or support to absorb and/or distribute forces imparted to spinal column 2. Disc degeneration, for example, may result when the inner gel-like center begins to dehydrate, which may result in a degenerated disc 8 having decreased thickness. This decreased thickness may limit the ability of degenerated disc 8 to absorb shock which, if left untreated, may result in pain and/or vertebral injury.

While pain medication, physical therapy, and other non-operative conditions may alleviate some symptoms, such interventions may not be sufficient for every patient. Accordingly, various procedures have been developed to surgically improve patient quality of life via abatement of pain and/or discomfort. Such procedures may include, discectomy and fusion procedures, such as, for example, anterior cervical interbody fusion (ACIF), anterior lumbar interbody fusion (ALIF), direct lateral interbody fusion (DLIF) (also known as XLIF), posterior lumbar interbody fusion (PLIF), and transformational lumbar interbody fusion (TLIF). During a disectomy, all or a portion of a damaged disc (for example, degenerated disc 8, shown in FIG. 1), is removed via an incision, typically under X-ray guidance.

Following the discectomy procedure, a medical professional may determine an appropriate size of an interbody device 9 (shown in FIG. 2) via one or more distractors and/or trials of various sizes. Each trial and/or distractor may be forcibly inserted between adjacent vertebrae 4. Upon determination of an appropriate size, one or more of an ACIF, ALIF, DLIF, PLIF, and/or TLIF may be performed by placing an appropriate interbody device 9 (such as, for example, a cage, a spacer, a block) between adjacent vertebrae 4 in the space formed by the removed degenerated disc 8. Placement of such interbody devices 9 within spinal column 2 may prevent spaces between adjacent vertebrae 4 from collapsing, thereby preventing adjacent vertebrae 4 from resting immediately on top of one another and inducing fracture of vertebra 4, impingement of the spinal cord, and/or pain. Additionally, such interbody devices 9 may facilitate fusion between adjacent vertebrae 4 by stabilizing adjacent vertebrae 4 relative to one another. Accordingly, as shown in FIG. 2, such interbody devices 9 often may include one or more bone screws 11 extending through interbody device 9 and into adjacent vertebrae 4.

Often, following the removal of the distractor and/or trial, a medical professional must prepare one or more bores or holes in a vertebra 4 intended to receive the bone screws 11. Such holes may be formed with the aid of a separate drill guide positioned proximate or abutting vertebra 4 and inserting a drill therethrough. Alternatively, such holes may be formed free hand, without the use of a drill guide. Further, since spinal column 2 is subject to dynamic forces, often changing with each slight movement of the patient, such screw(s) 11 have a tendency to back out (for example, unscrew) and/or dislodge from interbody device 9, thereby limiting interbody device's 9 ability to stabilize adjacent vertebrae 4, and consequently, promote fusion. Additionally, if screw(s) 11 back out and/or dislodge from the interbody device 9, they may inadvertently contact, damage, and/or irritate surrounding tissue. Further, interbody device 9 is commonly comprised of a radiopaque material so as to be visible in situ via x-ray and other similar imaging modalities. However, such materials may impede sagittal and/or coronal visibility, thereby preventing visual confirmation of placement and post-operative fusion.

Thus, there remains a need for improved interbody devices, associated systems, and methodologies related thereto.

SUMMARY OF THE DISCLOSURE

The present disclosure includes examples that relate to, among other things, intradiscal, extradiscal, interdiscal implants. The interbody devices and systems (including, cages and/or plate devices) disclosed herein may be used as, for example, but not limited to, standalone devices, anterior lumbar interbody fusion devices, standalone anterior low-profile plating devices, an interlocking of standalone devices to create hybrid devices, modular systems to allow interchangeability, and the like. Each of the examples disclosed herein may include one or more features described in connection with any of the other disclosed examples.

According to an aspect of the disclosure, an interbody system is provided for implanting between vertebrae. The interbody system comprises a cage having a cage body that includes a graft chamber having a volume that receives graft material, a first sagittal wall having an inner wall surface that forms a first sagittal portion of the graft chamber, a second sagittal wall having an inner wall surface that forms a second sagittal portion of the graft chamber, an aft-wall having an inner wall surface that forms a posterior coronal portion of the graft chamber, and a wall, membrane that forms an anterior coronal portion of the graft chamber. The interbody system may further comprise an interbody device that includes an aperture that receives a bone fastener, wherein the wall membrane interacts with the bone fastener.

The wall membrane may interact with the bone fastener to bend as result of a force applied by the bone fastener to a portion of the wall membrane, thereby providing directional support to the bone fastener.

The wall membrane may interact with the bone fastener to bend as result of a force applied by the bone fastener to reduce the volume of the graft chamber, thereby forcing graft material from the graft chamber.

The wall membrane may comprise a slit. The slit may facilitate bending of a portion of the wall membrane as a result of a force applied to said portion of the wall membrane. The slit may receive and guide the bone fastener.

The wall membrane may comprise a thin sheet that is integrated with or attached to the cage body, a thin mesh that is integrated with or attached to the cage body, a thin screen that is integrated with or attached to the cage body, or a beams screen that is integrated with or attached to the cage body.

The sagittal wall of the cage body may comprise a recessed wall portion located proximate to the wall membrane. The sagittal wall may comprise a grip interface that contacts and engages a grip interface provided on the interbody device to secure the cage to the interbody device.

The graft chamber may comprise a first chamber width portion that holds graft material, and a second chamber width portion that holds graft material, wherein the width of the first chamber width portion is greater than the width of the second chamber width portion.

The interbody interbody device may comprise two or more apertures that receive two or more respective bone screws.

The cage body may comprise a plate guide that engages a cage guide provided on the interbody device to facilitate proper positioning and alignment of the cage with respect to the interbody device.

The cage body may comprise a plate engager that aligns with a cage engager provided on the interbody device to secure the cage body to the interbody device.

According to a further aspect of the disclosure, an interbody system is provided for implanting between vertebrae that comprises a cage body having a pair of sagittal walls, an aft wall and a wall membrane that is made of a shape memory form material. The interbody system may further comprise an interbody device that attaches to the cage body, wherein the interbody device comprises an aperture that receives a bone fastener, and wherein the wall membrane bends under a force applied by the bone fastener.

According to a still further aspect of the disclosure, an interbody system is provided for implanting between vertebrae that comprises a cage having a cage body that includes a graft chamber having a volume that receives graft material, a sagittal wall that forms a portion of the graft chamber, and a wall membrane that forms another portion of the graft chamber. The interbody system may further comprise an interbody device that includes an aperture that receives a bone fastener, wherein the wall membrane interacts with the bone fastener.

Additional features, advantages, and embodiments of the disclosure may be set forth or apparent from consideration of the detailed description and drawings. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to help explain the principles of the disclosure. No attempt is made to show structural details of the disclosure in more detail than may be necessary for a fundamental understanding of the disclosure and the various ways in which it may be practiced. In the drawings:

FIGS. 13A-13C illustrate different views of an example of a interbody device, constructed according to the principles of the disclosure;

FIGS. 15A-15E illustrate different views of an interbody system that includes the cage of FIG. 4 and the interbody device of FIGS. 13A-13C;

Figure 1:
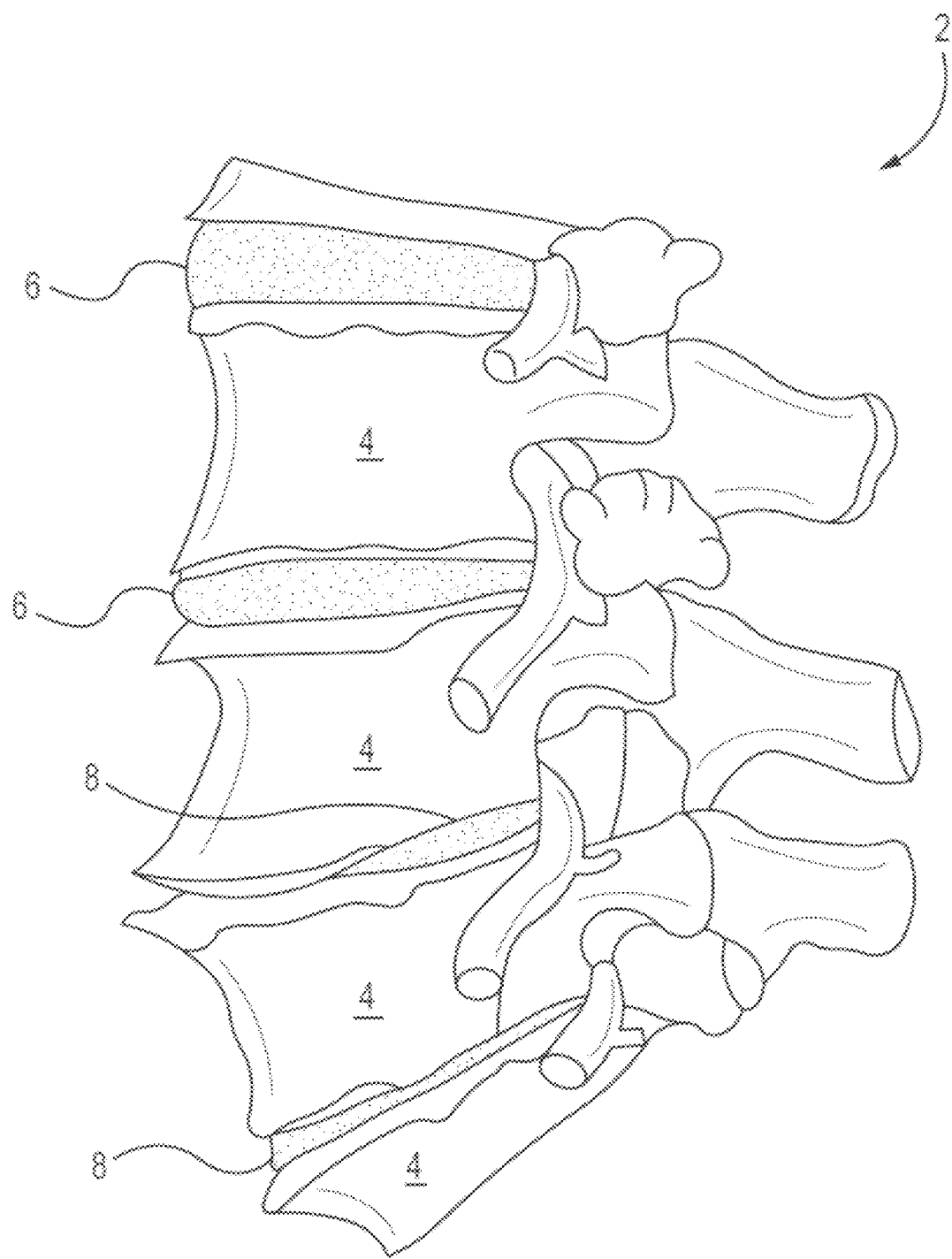
FIG. 1 illustrates a portion of a patient's spinal column.

The present disclosure is further described in the detailed description that follows.

DETAILED DESCRIPTION OF THE DISCLOSURE

The disclosure and the various features and advantageous details thereof are explained more fully with reference to the non-limiting embodiments and examples that are described and/or illustrated the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed a limiting the scope of the disclosure. Moreover, it is noted that like reference numerals represent similar parts throughout the several views of the drawings.

Figure 3:
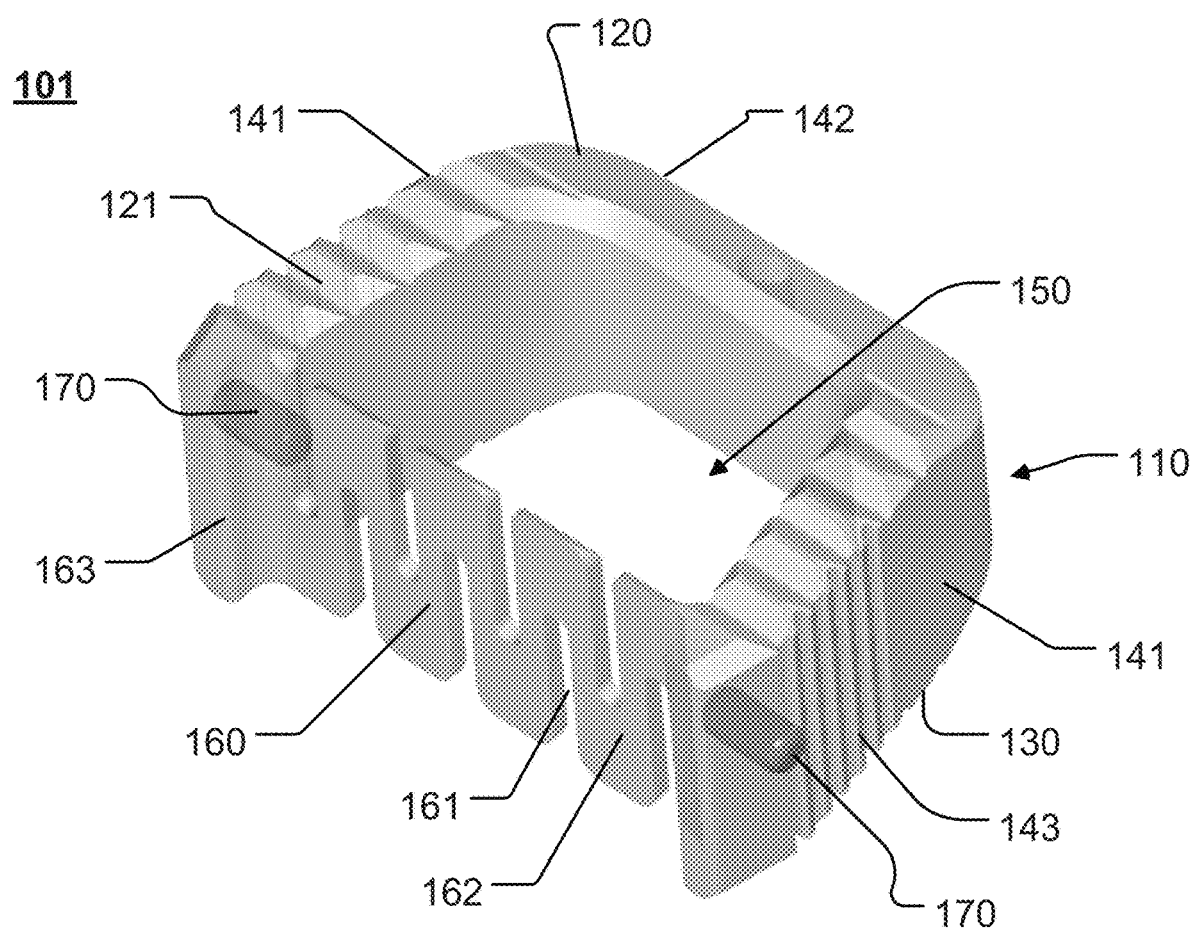
FIG. 3 illustrates a perspective view of an example of a cage, constructed according to the principles of the disclosure.

FIG. 3 illustrates an example of a cage (or interbody) device 101 that is constructed according to the principles of the disclosure. The cage 101 may include one or more features such as anti-migration and/or anchoring features, anti-rotation features, insertion tool features, reduced profile keel features, and the like. The cage 101 has a cage body 110 that may be formed as a single piece, or that may be assembled from multiple pieces. The cage body 110 may have a trapezoidal shape for proper anterior placement. The cage 101 may be made of one or more materials, including, for example, metal (e.g., titanium), metal alloy (e.g., titanium alloy), plastic, ceramic, elastomers, carbon fiber reinforced polymers, polyetheretherketone (PEEK), tricalcium phosphate, hyroxyaptaite, or the like, or any combination thereof. The cage 101 may have any shape, including, for example, a trapezoid, a square, a rectangle, an ellipse, a semicircle, or the like, or any combination of the foregoing, that may be implanted, for example, between a pair of adjacent vertebrae.

Referring to FIG. 3, the cage body 110 includes a pair of sagittal (or side) walls 141 and an aft-wall 142. The cage 101 may further include a fore-wall 160. The sagittal walls 141, aft-wall 142 and fore-wall 160 may form a chamber 150 that may receive and hold autologous bone, allograft bone, xenograft bone, bone graft material, osteoinductive material, blood tissue, or the like. The chamber 150 may have a large graft are to provide generous biological coverage. The inner surfaces of the sagittal walls 141, aft-wall 142 and/or fore-wall 160 may have a smooth surface or a pattern that may help in holding, for example, a bone graft material in the chamber 150, such as, for example, a roughened surface, or a pattern that increases the coefficient of friction with respect to the bone graft material in the chamber 150. One or more of the outer surfaces of the side walls 141 and/or aft-wall 142 may include a grip interface 143. The grip interface 143 may have a pattern (e.g., teeth, serrations, protrusions, or the like) that increases gripability and improves handling, for example, a surgeon's hand or instrument to securely grasp and hold the cage body 110 during implanting. The grip interface 143 may be configured to contact and engage a grip interface provided on a interbody device (for example, grip interface 2432 on the interbody device 240, shown in FIG. 13A), so as to secure the cage 101 to the interbody device.

The cage 101 may have a first surface 120 and a second surface 130. The first surface 120 may include a plurality of bone interface members 121, such as, for example, teeth, serrations, protrusions, which may have a shape that is, e.g., triangular, pyramidal, conical semispherical, rectangular, cylindrical, diamond, and/or irregular shapes, or the like. The first and second surfaces 120, 130 may have an aggressive pattern formed by the bone interface members 121 to resist expulsion. The first and second surfaces 120, 130, may be substantially the same or different. For instance, the first surface may include bone interface members 121 that have, for example, a pyramidal pattern and the second surface may include bone interface members (not shown) that have, for example, a pyramidal pattern and/or a semi spherical pattern. The bone interface members 121 engage with the bony surface of vertebral bodies in or near the treated area. The bone interface members 121 may be formed integrally with the surface 120 (or 130) and may vary in profile, distribution, size, and number. The configuration of the surface 120 (or 130), including bone interface members 121, should be sufficient to securely hold the cage 101 in the treated area after surgery while the treated area heals and undergoes fusion.

The fore-wall 160 may include a wall membrane 162, as seen in FIG. 1. The for-wall 160 may include one or more slits 161. The slits 161 may be formed in one or both of the superior or inferior directions (that is, in the directions normal to the surfaces 120, 130). If the slits 161 are formed in both the superior and inferior directions, then the slits 161 may be offset from each other, so as to form a snake-like pattern. (shown in FIG. 3). Alternatively (or additionally), the slits 161 may be formed so as to align with each other in the superior (or cranial) and inferior (or caudal) directions (shown FIG. 4). The wall membrane 162 may be made of a thin, flexible and/or malleable material. The wall membrane 162 may be made of an elastic memory material that resumes a default shape absent an external force, such as, for example, the default shape seen in FIG. 3 (or FIG. 4). The material may include titanium, titanium alloy, PEEK, or the like. The fore wall 160 may be constructed so as to be easily poked, breached, bent or penetrated by, for example, a hole preparation instrument (not shown), a bone fastener, or the like.

Figure 16A:
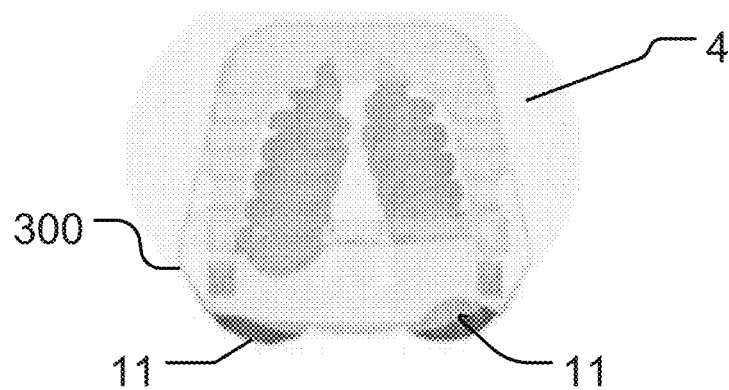
FIGS. 16A-16C illustrate an example of the interbody system of FIGS. 15A-15D installed between a pair of bony structures.
Figure 16B:
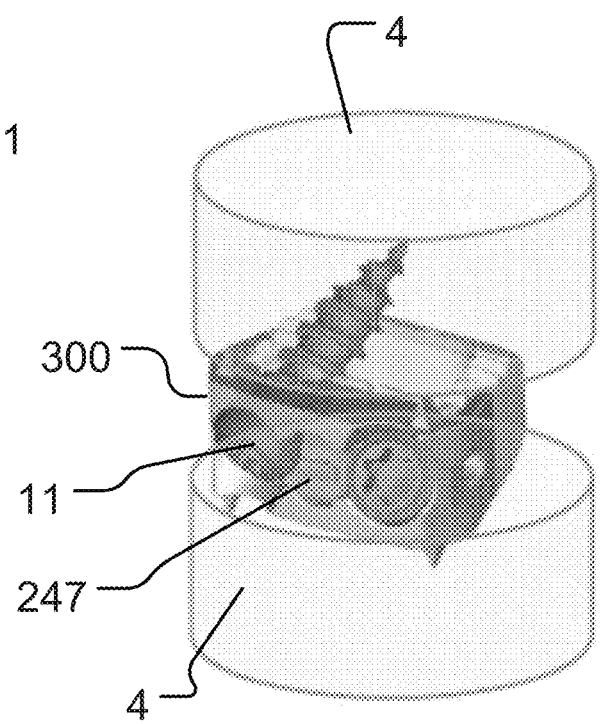

The wall membrane 162 may function to deflect and guide a bone fastener 11 to an anchoring positron in the adjacent bone structure, as seen in FIGS. 15D and 16B, thereby facilitating easier and better positioning of the bone fastener 11 during installation of an interbody system (e.g., interbody system 300 or 400, shown in FIGS. 15A-15E and 17B-17E). For instance, referring to FIGS. 15A and 15D, as a bone fastener 11 is inserted through an aperture 242, the distal end of the fastener 11 may contact the wall membrane 162 and, as the fastener 11 is moved toward the wall membrane 162, the upper (or lower) portion of the wall membrane may bend and deflect the fastener 11 upward (or downward) toward the anchor site on the adjacent vertebra 4 (shown in FIGS. 16B and 16C).

Further, when a graft material is located in the graft chamber 150, deflection of the bone fastener(s) 11 will result in portion(s) of the wall membrane 162 moving into the graft chamber 150 and reducing the space in the chamber 150, thereby, forcing graft material upward and/or downward out of the graft chamber 150 and into the spaces surrounding the cage 101, including packing the graft material into the area between the cage 101 and adjacent vertebrae 4 to better promote bone growth.

The cage 101 may include one or more radiopaque elements 170 to assist with alignment, positioning or placement of the cage 101 in a treated area. The radiopaque element(s) 170 may include, for example, a radiopaque tantalum bead, or the like. The cage 101 may be provided with one radiopaque element 170 at each of three corners of the cage 101 to facilitate radiographic implant positioning.

The cage 101 may include one or more plate interfaces 103. The plate interface 163 may be integrally formed with the cage body 110. The plate interface 163 may be constructed as an extension of the side wall 141. The plate interface 163 may be configured to correspond to and mate with (or engage) a corresponding cage interface (e.g., cage interface 2463, shown in FIG. 13C) provided on an interbody device (e.g., interbody device 240 shown in FIGS. 13A-13C). When mated to the cage interface, the plate interface 163 may provide a secure and snug fit, so as to properly align the interbody device and cage 101 with respect to each other. The plate interface 163 and cage interface (e.g., cage interface 2463, shown in FIG. 13C) may be constructed as a tongue and groove configuration, with one of the interfaces being formed as the tongue portion and the other interlace being formed as the groove portion.

Figure 4:
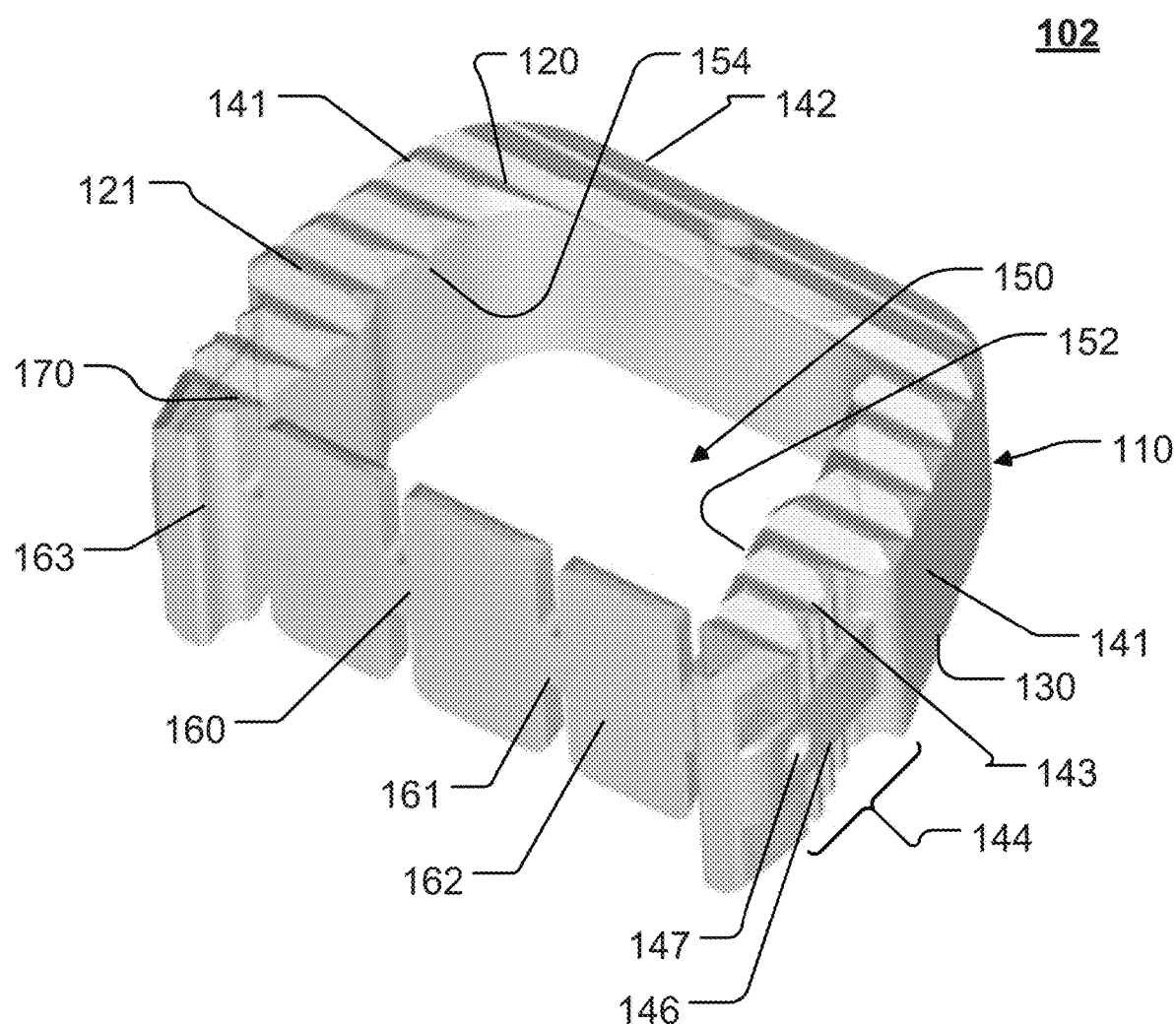
FIG. 4 illustrates a perspective view of another example of a cage, constructed according to the principles of the disclosure.

FIG. 4 illustrates a perspective view of another example of a cage (or interbody) device 102, constructed according to the principles of the disclosure. The cage 102 includes a cage body 110. The cage body 110 includes a pair of sagittal (or side) walls 141 and the aft-wall 142. The cage 102 further includes the fore-wall 160. The side walls 141 may include a pair of recessed wall portions 144 located near the fore-wall 160. The inner surfaces of the side walls 141, the aft-wall 142 and fore-wall 160 form the graft chamber 150. The cage 102 may be made of one or more materials, including, for example, metal (e.g., titanium), metal alloy (e.g., titanium alloy), plastic, ceramic, elastomers, carbon fiber reinforced polymers, polyetheretherketone (PEEK), tricalcium phosphate, hyroxyaptaite, or the like, or any combination thereof.

The graft chamber 150 may include a chamber-width portion 152 and a chamber-width portion 154. The width the of the chamber-width portion 152 may be less than the width of the chamber-width portion 154. Alternatively, the width of the camber-width portion 152 may be equal to or greater than the width of the chamber width portion 154. The chamber-width portion 152 may have a width formed between opposing inner wall surfaces of the side walls 141 by the inner wall surface of a plate interface region 144 on each of the side walls 141.

The plate interface region 144 of the side wall 141 may include the grip interface 143 and a plate guide 146. The wall plate interface region 144 may include a plate engager 147.

The plate guide 146 may be formed as, for example, a longitudinal track along the longitudinal axis of the side wall 141. The plate guide 146 may be configured to engage a corresponding cage guide (e.g., cage guide 2433, shown in FIGS. 13A, 13C) provided on an interbody device (e.g., interbody device 240, shown in FIGS. 13A, 13C), so as to facilitate proper positioning and alignment of the cage 102 with respect to the interbody device (e.g., interbody device 240 shown in FIGS. 13A-13C or interbody device 410 shown in FIGS. 17A-17E).

The plate engager 147 may be formed as an aperture (e.g., a semi-spherical recess, a dented-in portion, an opening that extends from the outer surface to the inner surface of the wall 141, or the like) or as a protrusion (e.g., a semi-spherical bump, or the like). The plate engager 147 may be positioned and configured to align with a cage engager on an interbody device (e.g., cage engager 2431 on interbody device 240, shown in FIG. 13A).

As seen in FIGS. 3 and 4, the wall membrane 162 may be formed integrally as part of the cage, or the wall member 162 may be attached to ends of the walls 140 (shown in FIGS. 5A-5E).

Figure 5A:
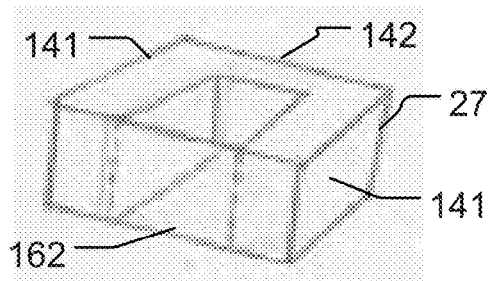
FIGS. 5A-5F illustrate examples of cages, constructed according to the principles of the disclosure.
Figure 5D:
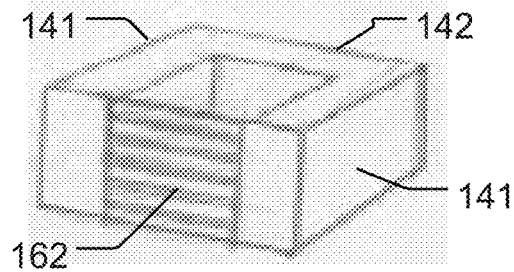
Figure 5B:
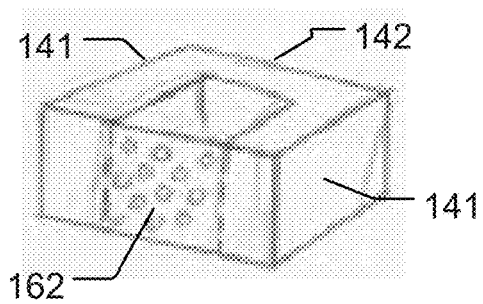
Figure 5E:
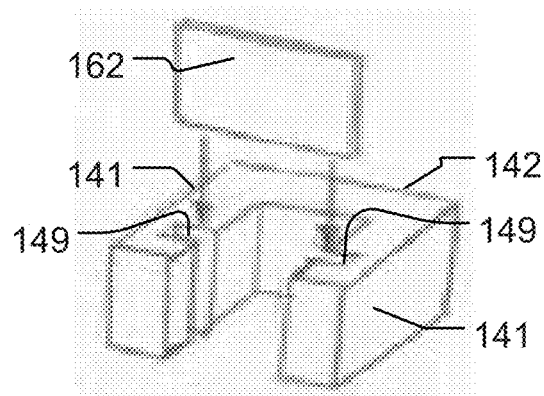
Figure 5C:
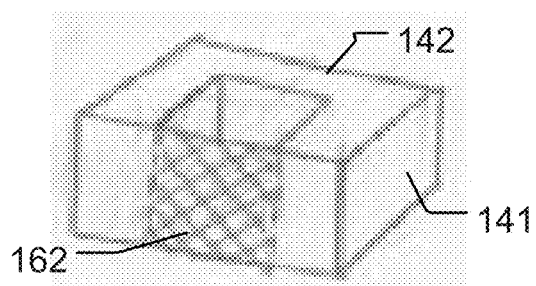
Figure 5F:
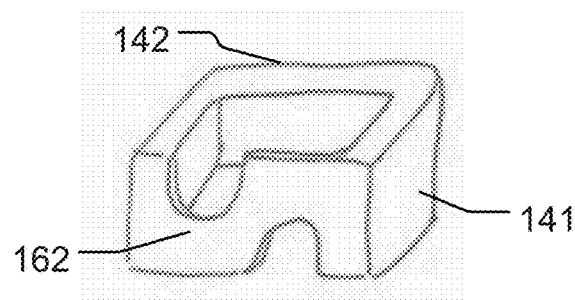

FIGS. 5A-5F illustrate examples of cages with different wall membranes 162, constructed according to the principles of the disclosure. As seen, FIG. 5A illustrates an example with the wall member 162 formed as a thin sheet that may be integrated with a cage body 27; FIG. 5B illustrates an example of the wall membrane 162 formed as a thin mesh, which may be integrated with or attached to the cage body 27. FIG. 5C illustrates an example of the wall membrane 162 formed as a thin screen, which may be integrated with or attached to the cage body 27; FIG. 5D illustrates an example of the wall membrane 162 that may be formed as a beams screen, which may be integrated with or attached to the cage body 27; FIG. 5E illustrates an example of attaching the wall membrane 162 by aligning and inserting ends of the wall member 162 into corresponding receiver tracks 149 that may be formed in the inner sides of the walls 141; and, FIG. 5F illustrates an example where the wall membrane 162 does not interact with bone fastener(s). The cage body 27 may be substantially the same as the cage body 110 (shown in FIG. 3 or 4).

FIGS. 6A-6F illustrate further examples of cages, constructed according to the principles of the disclosure, which may be used to reduce inventory by providing a cage that may adjust angle of lordosis. As seen in the illustrations, the cage may include the cage body 27 with an angle adjustment system, which may include an angle adjustment slit 1412 formed longitudinally in the side walls 141 and aft-wall 142, and an angle adjustment insert 1413 (shown in FIGS. 6A-6E), or an angle adjustment hinge 1417 (shown in FIG. 6F). The cage body 27 may be made of a material, such as, for example, a shape memory material that reverts to a particular configuration in the absence of any external force (shown in FIG. 6C).

Figure 6A:
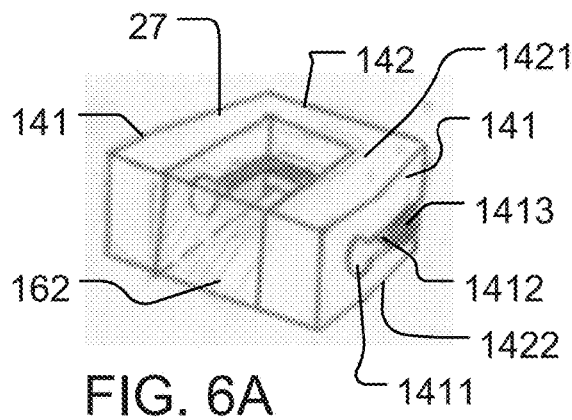
FIGS. 6A-6F illustrate further examples of cages, constructed according to the principles of the disclosure.

Referring to FIG. 6A, the cage body 27 may be formed with an angle adjustment slit 1412 in each of the side walls 141 and the aft-wall 142. The angle adjustment slit 1412 may be formed longitudinally along the longitudinal axis of the side wall 141 and the aft-wall 142, thereby separating the cage body 27 into a superior cage body portion 1421 and an inferior cage body portion 1422. The end portions of the superior cage body portion 1421 and the inferior cage body portion 1422 that are formed by the aft-wall 142 are configured to move toward or away from each other, thereby allowing for adjustment of angle of lordosis. The adjustment angle $\Theta$ (shown in FIG. 6E) may be defined and adjusted by, for example, inserting (or removing) the adjustment insert 1413 in one or both of the angle adjustment slits 1412. The adjustment angle may be varied and set by moving (e.g., incrementally) the adjustment insert 1413 along the angle adjustment slits) 1412.

The angle adjustment slit(s) 1412 may have a substantially uniform width along its entire length, or the width may vary along the length of the angle adjustment slit 1412 (e.g., increasing or decreasing). The adjustment insert 1413 may include, for example, a rod, a block or any other shape without departing from the scope or spirit of the disclosure. The diameter or height of the adjustment insert 1413 may vary to provide varying angles of adjustment. The length of the adjustment insert 1413 may vary depending on the dimensions of the cage body 27. The cage body 27 may include a fulcrum aperture 1411, which may provide added flexibility to the cage body 27 with angle adjustment slits 1412. The fulcrum aperture 1411 may have a diameter (or width that is greater than the width of the portion of the angle adjustment slit 1412 nearest to the fulcrum aperture 1411.

Figure 6D:
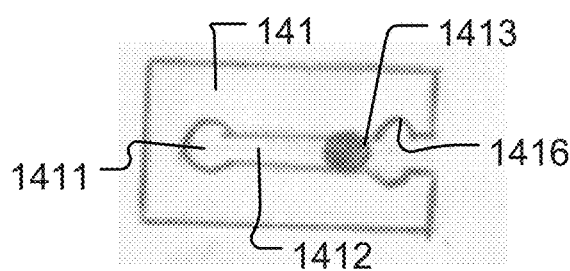
Figure 6B:
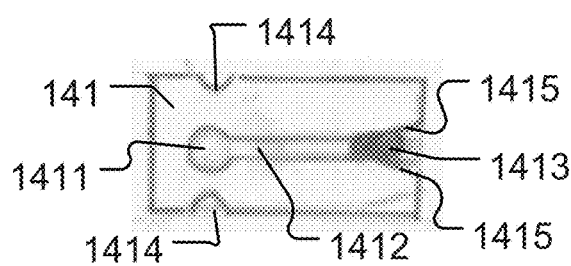

FIG. 6B shows the cage body 27 provided, with flexing cutouts 1414 above and/or below the fulcrums aperture 1411. The flexing cutouts 1414 are formed to provide added flexibility to the cage body 27 with respect to the cage body portions 1421, 1422. The portion of the adjustment slit 1412 in the aft-wall 142 may include tapered wall portions 1415, so as to facilitate easier installation of the adjustment insert 1413 into the adjustment slit 1412.

Figure 6E:
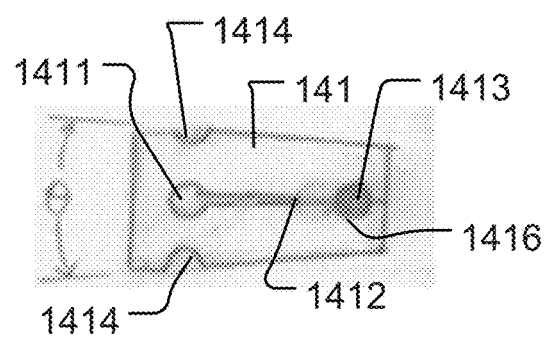
Figure 6C:
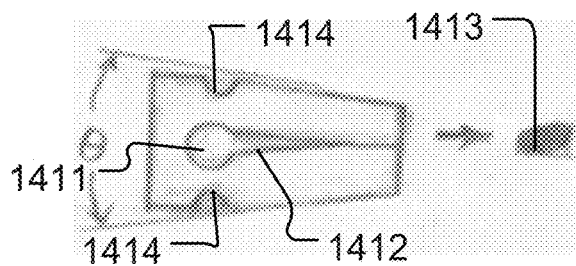

FIG. 6C shows the cage body 27 with the adjustment insert 1413 removed from the adjustment slit 1412. In this example, the cage body 27 is formed of a memory-form material that reverts to a maximum adjustment angle in the absence of an external force. The angle $\Theta$ may be adjusted by inserting the adjusting insert 1413 into the adjustment slit 1412. In this regard, the cage body 27 may include the tapered wall portions 1415 so as to facilitate easier insertion of the adjusting insert 1413 into the adjustment slit 1412.

FIGS. 6D and 6E illustrate examples of the cage body 27 provided with an insert lock 1416. As seen, the insert lock 1416 may be a notch, such as, for example, a notch formed longitudinally along the adjustment slit in the aft-wall 142. The notch may be formed longitudinally in the aft-wall 142 and/or transversely across the side wall(s) 141 (i.e., across the width of one or both side walls 141). The notch may have a shape such as, for example, a semi-circle, a square, a rectangle, or the like. The notch may be formed in either or both of the superior and inferior body portions 1421, 1422. The insert lock 1416 may have a height (or diameter) that is substantially equal to the height (or diameter) of the adjustment insert 1413. Alternatively, the height (or diameter) of the insert lock 1416 may be greater or less than the height (diameter) of the adjustment insert 1413. The insert lock 1416 may function to securely hold the adjustment insert 1413, so as to provide a predetermined adjustment angle $\Theta$. Although not shown, the adjustment slit 1412 may be provided with a plurality of insert locks 1416 along the length of the slit, each of which may be formed to provide a different, predetermined adjustment angle $\Theta$, which may be determined by the location of the insert lock 1416 along the adjustment slit, the height (or diameter) of the insert lock 1412, or the shape of the insert lock 1412.

Figure 6F:
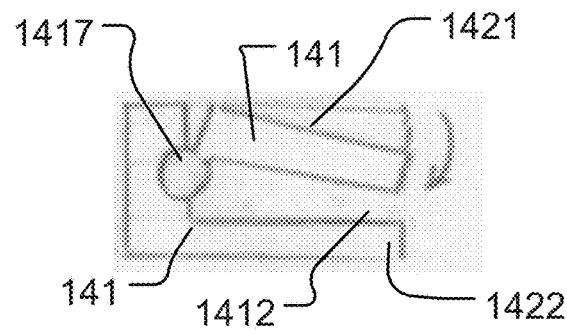

FIG. 6F shows an example of a cage body 27 provided with a hinge 1417. As seen, the superior cage body portion 1421 and the inferior cage body portion 1422 may be connected by a hinge 1417 provided in the cage body 27 at the end opposite the aft-wall 142. The hinge 1417 is configured to permit one or both of the cage body portions 1421, 1422 to pivot toward or away from each other, thereby adjusting the angle $\Theta$.

Figure 7A:
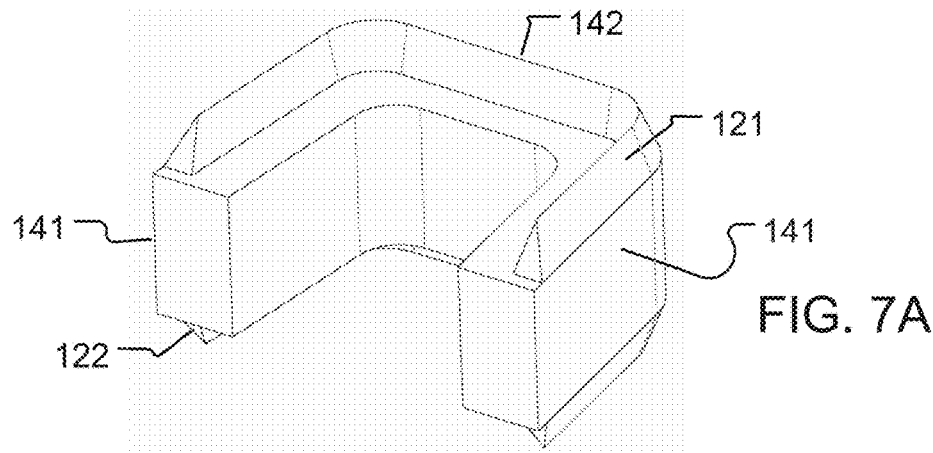
FIGS. 7A-7B illustrate different views of an example of a cage, constructed according the principles of the disclosure.
Figure 7B:
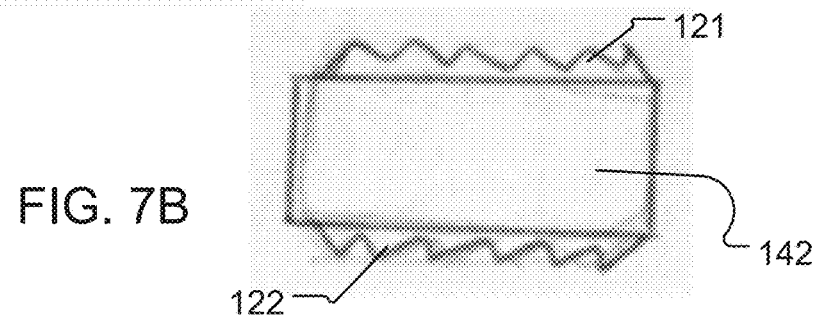

FIGS. 7A-7B illustrate different views of a cage body provided with a pair of anchor rims 121, 122. Although shown with two anchor rims 121, 122, the cage body may be provided with only a single anchor rim 121 (or 122) provided on one of the superior or inferior surfaces of the cage body. Alternatively (or additionally), a plurality of anchor runs 121 (or 122) may be provided on the same surface of the cage body. The anchor rim 121 (or 122) may be continuous (shown in FIG. 7A) or discontinuous (not shown, such as, e.g., in one or more segments). The anchor rim 121 (or 122) may have a consistent geometry (shown in FIG. 7A) or have a variable geometry (shown in FIG. 7B) geometry may be, for example, a serrated pattern, a saw-tooth pattern, or any other pattern that may aggressively contact and engage honey matter.

Figure 8:
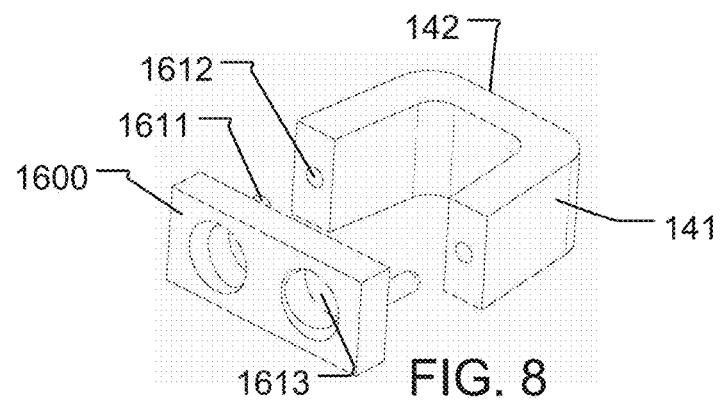
FIG. 8 illustrates and an example of an interbody system, constructed according to the principles of the disclosure.

FIG. 8 illustrates an example or interbody system, constructed according to the principles of the disclosure. The interbody system may include the cage body 27 and an interbody (or plate) device 1600. The interbody system may further include a wall membrane 102 (not shown), which may be positioned at, for example, the anterior portion of the cage body 27, and proximate the inner wall surface of the interbody device 1600. The interbody device 1600 may be attached to the cage body 27 by an attachment mechanism, such as, for example, a bonding or adhesive material, a pressure fit, tongue and groove, spring clamp, joining screws, or the like.

The interbody system of FIG. 8 is an example of a pressure fit attachment mechanism, which includes one or more receivers (e.g., openings) 1612 provided on the cage body 27, and corresponding one or more protrusions 1611 on the interbody device 1600. Alternatively, the one or more receivers 1612 may be provided on the interbody device 1600 and the corresponding c or more protrusions 1611 may be provided on the cage body 27. As seen, the receivers 1612 may be formed to align with and securely receive the corresponding protrusions 1611 when the interbody device 1600 and rage body 27 are pressed toward each other, so as to securely fasten the interbody device 1600 to the cage body 27.

Figure 9A:
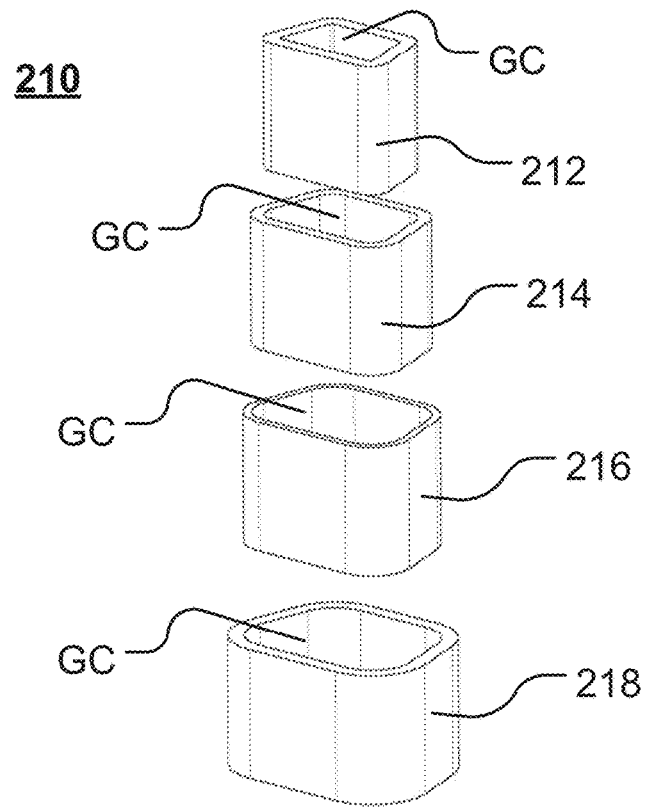
FIGS. 9A-9C illustrate examples of a modular cage, constructed according to the principles of the disclosure.
Figure 9B:
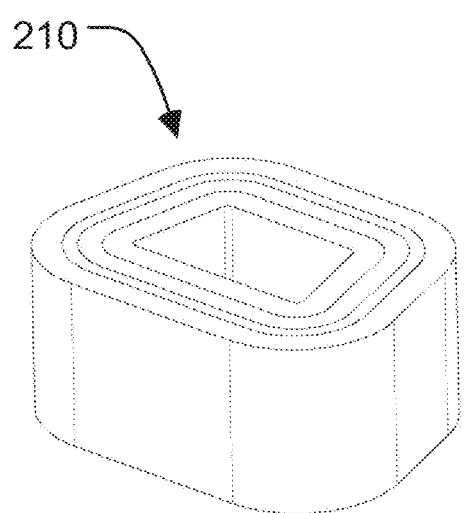
Figure 9C:
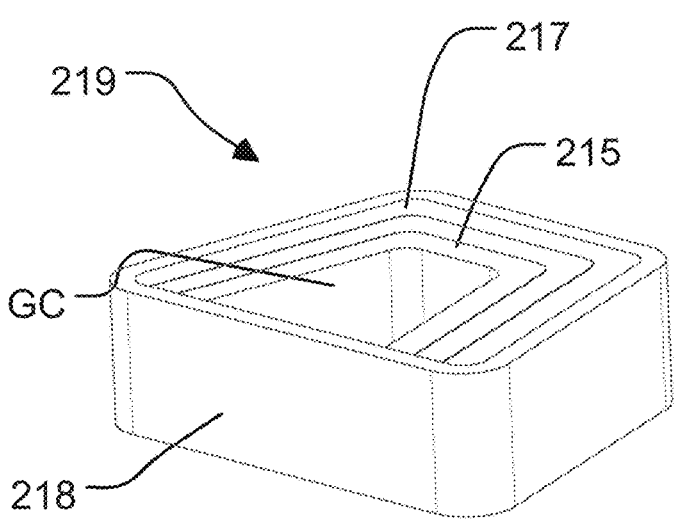

FIGS. 9A-9C illustrate examples of a modular cage system 210, constructed according to the principles, of the disclosure. The shell-in-shell configuration of the modular cage system 210 can be used to minimize inventory of parts. The modular cage system 210 provides an adjustable footprint, where in a closed loop geometry may be implemented (shown in FIGS. 9A-9b), an open loop geometry may be implemented (not shown), or a hybrid closed-open loop geometry may be implemented (shown FIG. 9C).

Referring to FIGS. 9A-9B, the modular cage system 210 comprises a plurality of closed loop cage bodies 212, 214, 216, 218. Each of the cage bodies 212, 214, 216, 218, may have substantially the same shape and varying (e.g., increasing or decreasing) (e.g. height, width, length, surface angle (e.g., angle of superior surface along posterior-anterior and/ or lateral directions of cage body, and/or angle of inferior surface along posterior-anterior and/or lateral directions of cage body)), so that the cage bodies may be nested together to form a unitary configuration of the modular cage system 210, as seen in FIG. 9B, by nesting one inside another. One or more of the cage bodies 212, 214, 216, 218 may have a different shape and/or size than the other cage bodies. The cage bodies may be selected and nested together to form a cage system 210 that matches the size, shape, contours, etc. of the adjacent vertebrae surfaces. Each of the cage bodies 212, 214, 216, 218 may be made of a single material or combination of various materials for, for example, radio-opaque and/or strength effects. The cage bodies 212, 214, 216, 218 may be made of the same or different materials. The modular cage system 210 may include, for example, two, three, four, or more cage bodies.

The cage bodies 212, 214, 216, 218 each have a graft chamber GC, whose dimensions and position may be varied by varying the thicknesses and/or shapes of the walls of the respective case body. For instance, by making one of the four walls of the cage body 212 much thicker than the other three walls, the center of the graft chamber GC may be shifted away from the thicker wall. Further, by altering the inner contours of the walls of a cage body, the shape of the graft chamber GC may be selectively determined. The outer contours of the walls of one or more of the cage bodies 212, 214, 216, 218 may be varied to form cage bodies based on the particular anatomy of a patient.

Referring to FIG. 9C, a hybrid modular cage system 219 comprises a pair of open loop cage bodies 215, 217 nested in the closed loop cage body 218. The open loon cage bodies 215, 217 may each be formed with three walls, as seen in the illustration. Each of the cage bodies 215, 217, may have substantially the same shape and increasing (or decreasing) size, so that the cage bodies may be nested together to form a unitary configuration of the modular cage system 219, as seen in FIG. 9C, by nesting one inside another. The cage body 218 may have substantially the same (or different) shape as the open loop cage body 215 and/or 217, so as to receive and hold each of the cage bodies 215, 217 in the graft chamber GC of the cage body 218. One or more of the cage bodies 215, 217, 218 may have a different shape than the other cage bodies. Each of the cage bodies 215, 217, 218 may be made of a single material or combination of various materials for, for example, radio-opaque and/or strength effects. The cage bodies 215, 217, 218 may be made of the same or different materials.

One or more of the cage bodies 215, 217 may be nested in the cage body 218 to modify the dimensions, position and or shape, of the graft chamber GC in the cage body 218. By selecting wall dimensions and shapes of each of the cage bodies 215, 217, and nesting the cage bodies 215, 217 in a predetermined direction, the dimensions, position and/or shape of the graft chamber GC may be selectively determined. The predetermined direction may comprise, for example, the open end of the cage body 215 facing in the same or a different direction than the open end of the cage body 217. As seen in FIG. 9C, the open ends of the cage bodies 215, 217 may be positioned in the same direction, so as to position the center of the graft chamber GC toward the open end of the cage bodies 215, 217, when nested in the configuration seen in FIG. 9C. By making one of the walls of a cage body much thicker than the other three walls, the center of the graft chamber GC may be shifted away from the thicker wall. Further, by altering the inner contours of the walls of a cage body, the shape of the graft chamber GC may be selectively determined. The outer contours of the walls of one or more of the cage bodies 215, 217, 218 may be varied to form cage bodies based on the particular anatomy of a patient.

Figure 10:
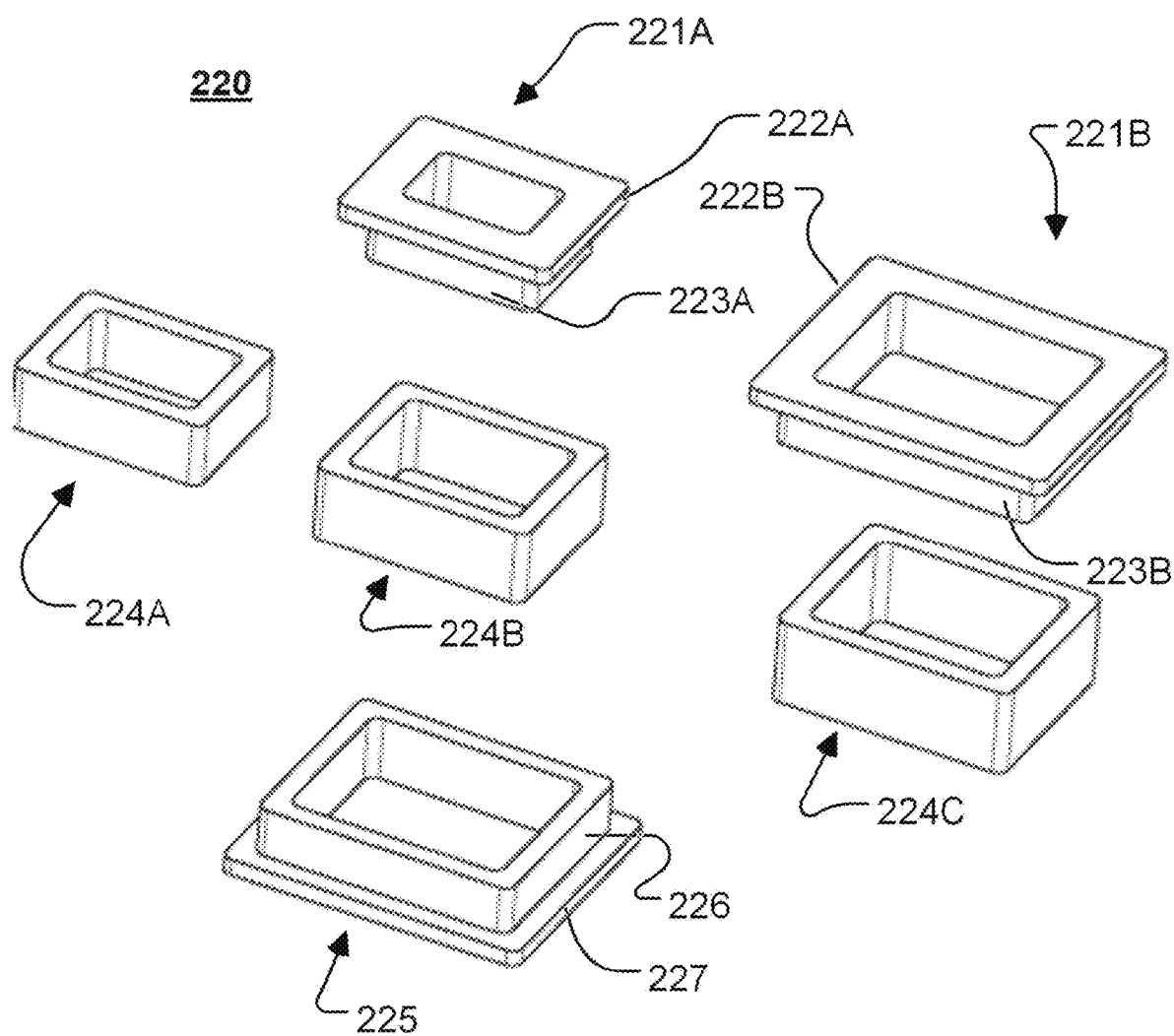
FIG. 10 illustrates further examples of a modular cage, constructed according to the principles of the disclosure.

FIG. 10 illustrates an example of modular cage system 220, constructed according to the principles of the disclosure. The modular cage system 220 may comprise a plurality of closed loop cage bodies 224A, 2248, 224C. The modular cage system 220 may, instead, include ail open loop cage bodies (not shown), or a hybrid system of open and closed loop cage bodies (not shown). The modular cage system 220 may further include one or more end caps 221A, 2215, 225. Each of the cage bodies 224A, 2248, 224C, may have substantially the same shape with varying (e.g., increasing or decreasing) size (e.g., height, width, length, surface angle (e.g., angle of superior surface along posterior-anterior and/ or lateral directions of cage body, and/or angle of inferior surface along posterior-anterior and/or lateral directions of, cage body)), as seen in FIG. 10, so that the cage bodies 224A, 2248, 224C may be interchangeably used with one or more of the end caps 221A, 221B, 225. One or more of the cage bodies 224A, 224B, 224C may have a different shape than the other cage bodies. Each of the cage bodies 224A, 224B, 224C and/or the end caps 221A, 221B, 225 may be made of a single material or combination of various materials for, for example, radio-opaque and/or strength effects. The cage bodies 224A, 224B, 224C and/or the end caps 221A, 221B, 225 may be made of the same or different materials.

The cage bodies 224A, 224B, 224C may have any shaper that may be implemented in an application between vertebral bodies, as will be understood by those skilled in the art. For instance, the cage bodies 224A, 224B, 224C may have a trapezoidal shape, with the side walls tapered inward in the posterior direction (e.g., shape of cage body 102 shown in FIG. 4), or the shape of the cage bodies 224A, 224B, 224C may be a square, rectangular, elliptical, circular, semicircular, or the like. The end caps 221A, 221B, 225 may have a shape that matches the shape of the cage bodies 224A, 224B, 224C.

As seen in FIG. 10, the end caps 221A, 221B, 225 may each include an insert portion 223A, 223B, 226, respectively, and/or a rim portion 222A, 222B, 227, respectively. For instance, referring to the end cap 221A with the understanding that the description equally applies to the end caps 221B and 225, the end cap 221A includes an insert portion 223A that may be inserted into the opening of the cage body 224A (or 224B or 224C), and a rim portion 222A that may function as a stop and/or cap for the cage body 224A (or 224B or 224C). The thickness, size and/or shape of the wall portions that form the insert portion 223A may be predetermined so as to selectively determine the position, shape, and/or size of the graft chamber in the cage body 224A (or 224B or 224C). For instance, the walls of the insert portion 223A may be varied in terms of size and shape, including, for example, height, width, length, surface angles, so as to determine the shape, position and size of the graft chamber in the cage body 224A (or 224B or 224C) when the end cap 221A is attached to the cage body 224A.

Figure 2:
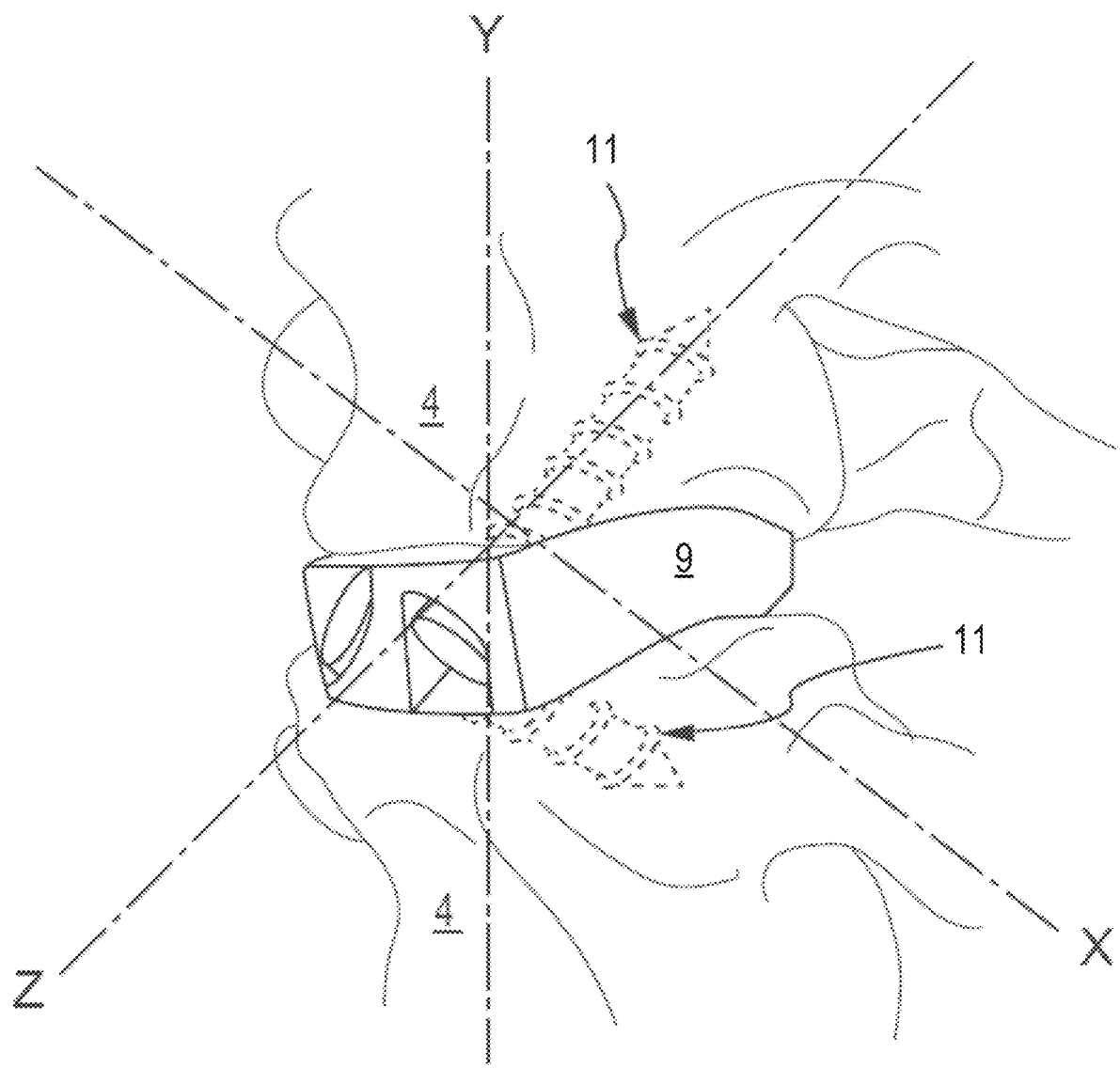
FIG. 2 illustrates an inter body device positioned within the patient's spinal column.

Similarly, the thickness, size and/or shape of the rim portion 222A may be varied to, for example, match anatomical requirements for particular applications of the cage system. For instance the height of the walls that form the rim portion 222A may be decreased (or increased) in the posterior (or anterior) direction, so as to provide better fit in vertebral interbody applications. The rim portion 222A may be configured to contact and engage a vertebral body. In this regard, the surface of the rim portion 222A may be contoured to match the shape of the vertebral body. The surface may include bone interface members (e.g., bone interface members 121, shown in FIG. 3) that may be configured to aggressively grip against the bony surface of the adjacent vertebral body (e.g., vertebral body 4, shown in FIG. 2).

Figure 11A:
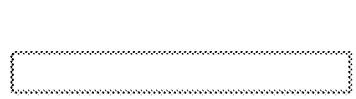
FIGS. 11A-11F show top views of examples of interbody devices, constructed according to the principles of the disclosure.
Figure 11B:
Figure 11C:
Figure 11D:
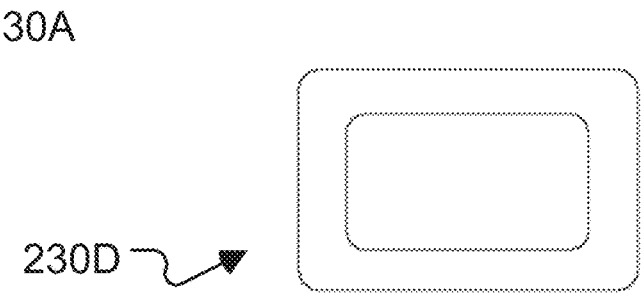
Figure 11E:
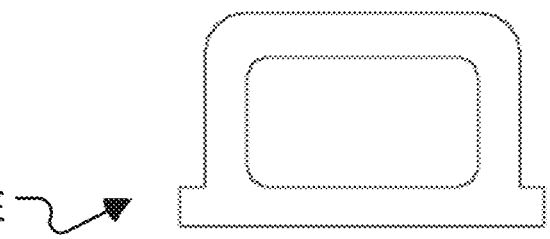
Figure 11F:
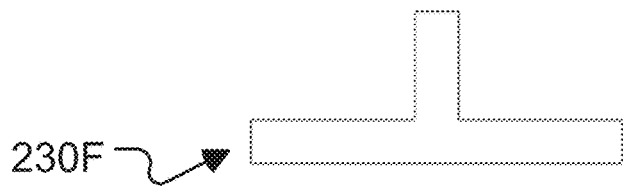

FIGS. 11A-11F show superior/cranial (or inferior/caudal) views of examples interbody devices 230A-230F, respectively, constructed according to the principles of the disclosure. More specifically, FIG. 11A illustrates the superior or cranial (or inferior or caudal) view of interbody device 230A that may be substantially planar, having an anterior surface (not shown and a posterior surface (not shown) with dimensions that are significantly greater than any, one of the wall surfaces, including the superior (or inferior) surface (shown in FIG. 11A), and sagittal (or side) surfaces (not shown); FIG. 11B illustrates the superior (or interior) view of interbody device 230B that has a C-shape (see also perspective views of examples of C-shape interbody devices in FIGS. 12A-12C) in the transverse plane; FIG. 11C illustrates the superior (or inferior) view of interbody device 230C that has a C-offset shape in the transverse plane; FIG. 11D illustrates the superior (or inferior) view of interbody device 230D that has a quadrilateral shape (see also perspective views of examples of trapezoid shape interbody devices in FIGS. 12D-12G) in the transverse plane; FIG. 11E illustrates the superior (or inferior) view of interbody device 230E that has a quadrilateral offset shape in the transverse plane; and FIG. 11F illustrates the superior (or inferior) view of an I-beam shape interbody device 230F in the transverse plane.

Figure 12A:
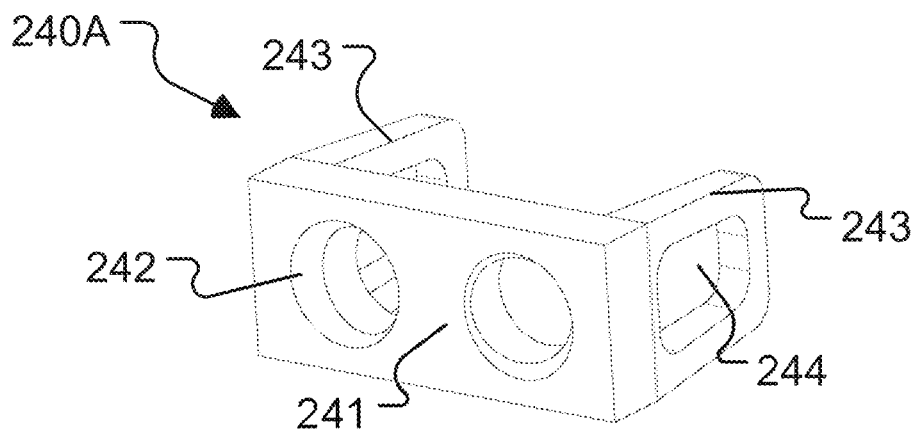
FIGS. 12A-12J illustrate examples of interbody devices, constructed according to the principles of the disclosure.
Figure 12B:
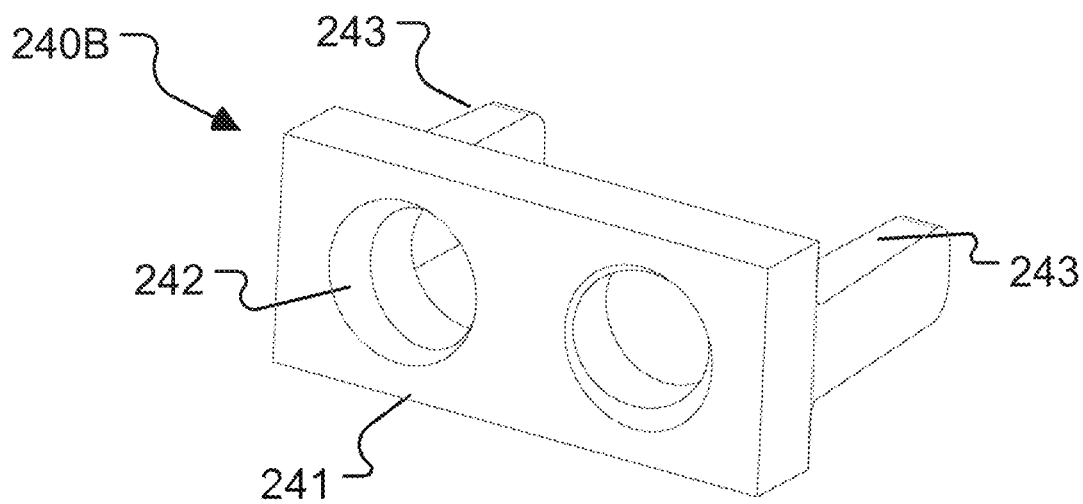
Figure 12C:
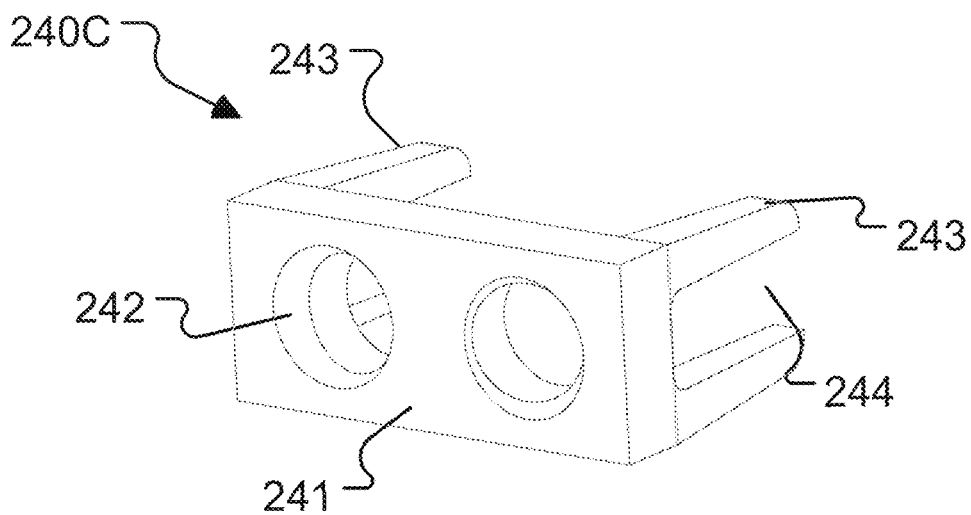
Figure 12D:
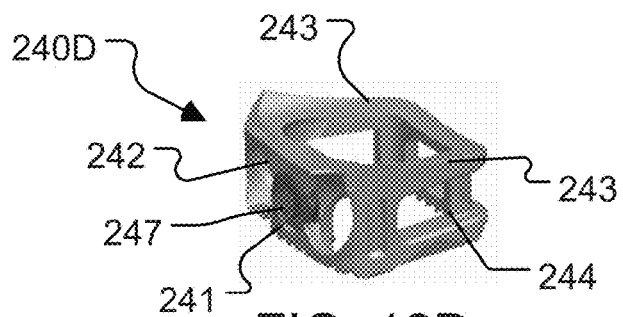
Figure 12E:
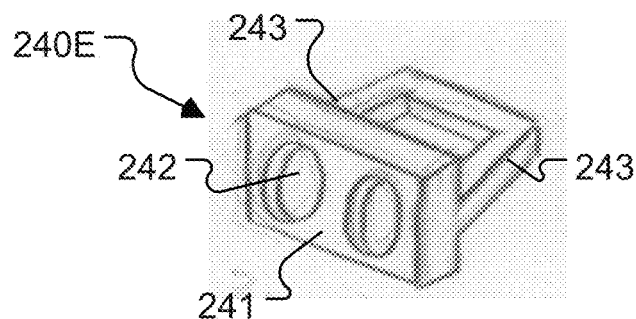
Figure 12F:
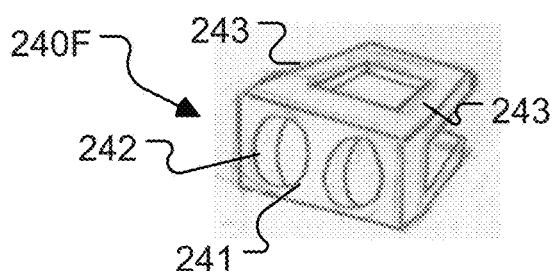
Figure 12G:
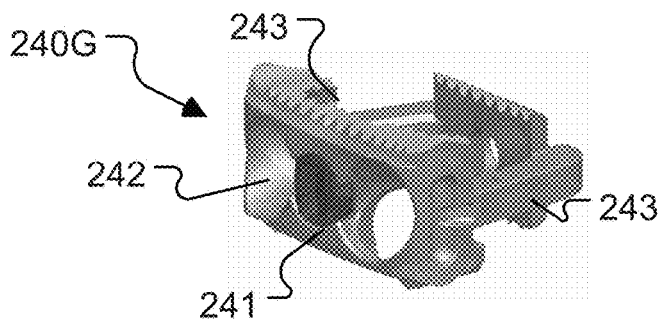
Figure 12H:
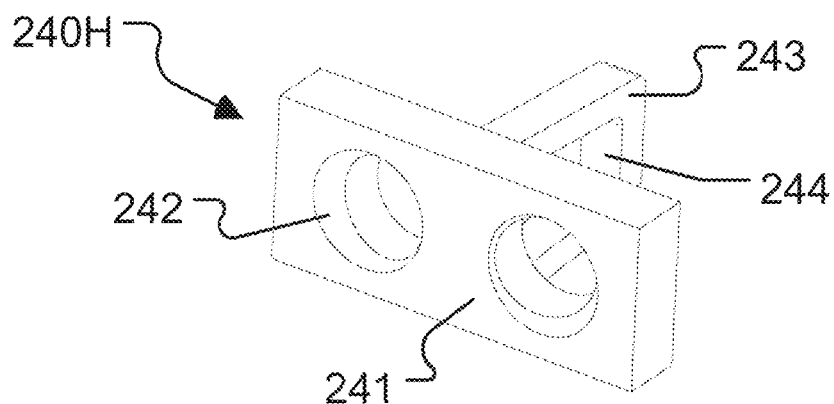
Figure 12I:
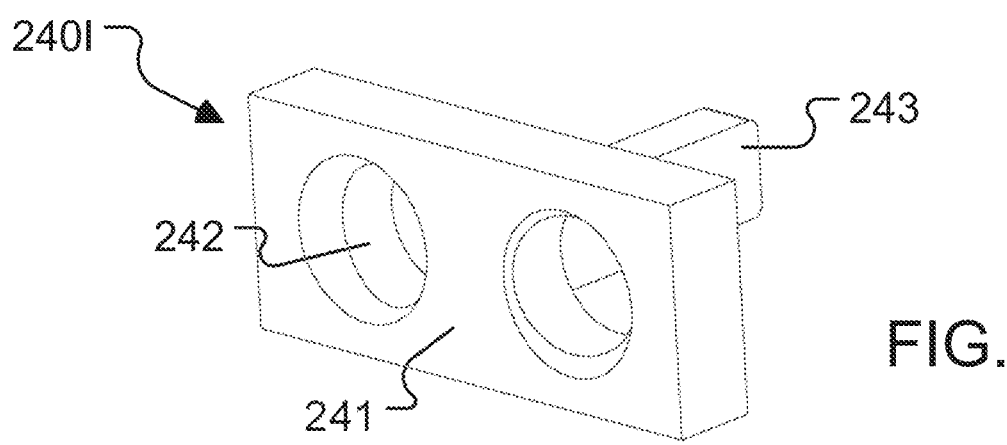
Figure 12J:
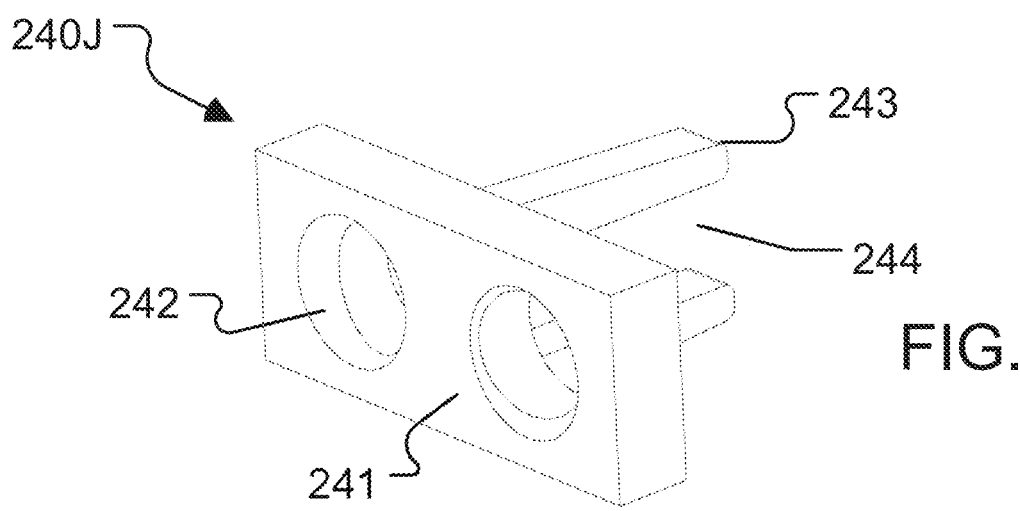

FIGS. 12A-12J illustrate perspective views of examples of interbody devices 240A-240J, respectively, constructed according to the principles of the disclosure. More specifically, FIGS. 12A-12C illustrate perspective views of examples of C-shape interbody devices 240A-240C, respectively; FIGS. 12D-12G illustrate perspective views of examples of transverse plane quadrilateral shape interbody devices 240D-240G, respectively; and FIGS. 12H-12J illustrate perspective views of examples of lateral I-beam shape interbody devices 240H-240J, respectively.

Referring to FIG. 12A, interbody device 240A may include a face 241 defining two apertures 242. The interbody device 240A may include a locking element 247, which is described in detail below. Various arrangements of interbody devices 240A may include one or more features configured to facilitate sagittal and/or coronal visibility. For example, a body or frame 243 of interbody device 240A may comprise a radiopaque material visible via x-ray or similar forms of imaging modalities. As such, frame 243 may enable accurate positioning and/or placement of interbody device 240A within and/or along spinal column 2 (shown in FIG. 1). Frame 243 may include any one or more features such as anti-migration and/or anchoring features, anti-rotation features, insertion tool features, reduced profile keel features, and the like. Additionally, frame 243 may define one or more openings and/or windows 244. Such windows 244 may remain empty and/or may be filled with radiolucent material such as tissue grafts as will be described in further detail below. Window(s) 244 may enable a medical professional to view and/or determine the level of post-operative fusion between interbody device 240A and patient bone and/or tissue. Frame 243 may define any appropriate arrangement, number, and configuration of window(s) 244. That is, as shown FIG. 12A, for example, interbody device 240A may comprise a standalone device having an open cage, or the interbody device 240A may be used as a plate device and attached to a cage (not shown). As shown in FIG. 12A, frame 243 may include a single window 244 on each lateral side. Each window 243 may be generally quadrilateral (e.g., square, rectangular, or trapezoidal). In some arrangements, a radiolucent structure, such as a graft containment sheath, may be disposed along one or more portions of frame 243. Indeed, such graft containment sheaths may substantially fill or encompass window 244 of one or more sides of frame 243. Accordingly, when the interbody device 240A is placed between two adjacent vertebrae 4 (shown in FIG. 1) under X-ray vision, window 244 remains radiolucent such that fusion within and/or through window 244 may be observed. In another arrangement, the interbody device 240B may comprise a standalone device having an open cage as seen in FIG. 12B, or it may be combined with a cage body (not shown), such as, for example the cage body 10 shown in FIG. 62 of U.S. patent application Ser. No. 14/956,084, filed Dec. 1, 2015, titled "Intervertebral Implants and Related Systems and Methods," the entirety of which is incorporated herein by reference.

Referring to FIGS. 12A and 12C, the interbody device 240C may have a similar arrangement to the interbody device 240A except that the window(s) 244 may be open on the posterior end, as seen in FIG. 12C.

Referring to FIGS. 12D and 12G, the interbody devices 240D and 240G may be substantially the same as the devices 10 shown in FIGS. 33 and 35, respectively, in U.S. patent application Ser. No. 14/956,084, filed Dec. 1, 2015, titled "Intervertebral Implants and Related Systems and Methods," which has been incorporated herein by reference.

FIGS. 12E-12F examples of interbody devices 240E, and 240F that have I-beam shape and a C-shape, respectively, in the sagittal plane. Both devices 240E and 240F have a closed trapezoidal shape frame 243 in the transverse plane.

FIGS. 12H-12J illustrate perspective views of examples of interbody devices 240H-240J that have an I-beam shape in the transverse plane, but varying arrangements in the sagittal plane. For instance, the interbody device 240H includes a frame 243 that has substantially quadrilateral (e.g., trapezoidal, rectangular, or the like) closed shape in the sagittal plane, which may include a window 244. The interbody device 240I includes a frame 243 that is substantially a rectangular rod in both the transverse and sagittal planes. The interbody device 2403 includes a frame 243 that has a C-shape in the sagittal plane, including an open-ended window 244.

FIGS. 13A-13C illustrate different views of an example of an interbody device 240 that is constructed according to the principles of the disclosure, including a perspective front or anterior view (FIG. 13A), a front or anterior view (FIG. 13B), and a perspective back or posterior view (FIG. 13C).

Referring to FIGS. 11A-13C, the interbody device 240 may include the anterior or front coronal face 24 and a posterior or back coronal face 248 (shown in FIG. 13C) defining a plurality (e.g., two) apertures 242 therebetween. The interbody device 240 may include a locking element 247. The interbody device 240 may be formed as a single piece (not shown), or it may be assembled from two or more pieces, such as, for example the frame 243 and the looking element 247.

Figure 14:
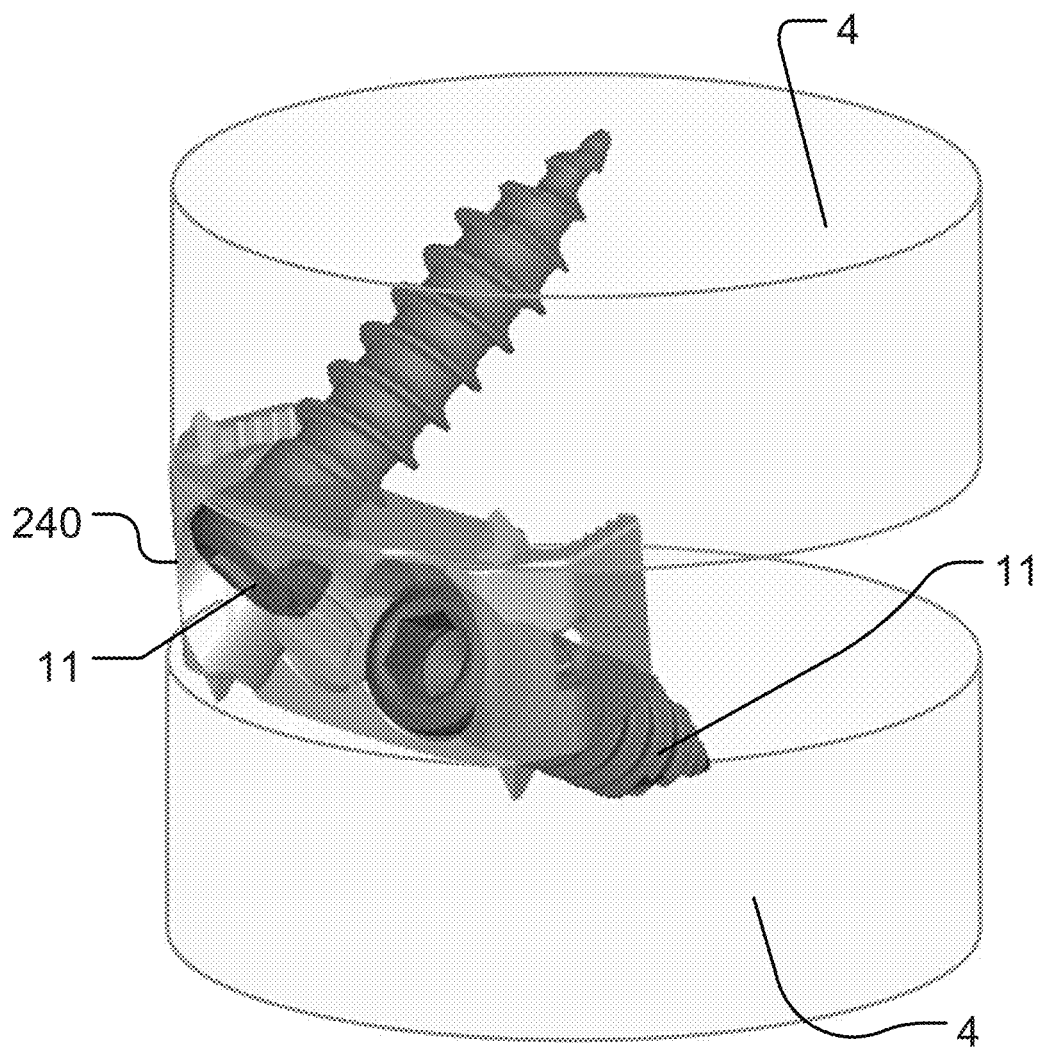
FIG. 14 illustrates an example of the interbody device of FIGS. 13A-13C installed between a pair of bony structures.

The aperture(s) 242 may have an angled opening so as to better guide a fastener 11 (shown in FIG. 14) as it is inserted in and through the aperture 242 into adjacent bone, thereby securing the fastener 11 in adjacent vertebra (shown in FIG. 14) for example, an optimal angle for securing the interbody device 240 to the vertebrae 4.

The locking element 247 may be similar in construction and manner of use as described, for example, in FIGS. 3A-22D, 33, 35, 7, 39, 55, 58-65B, or 69A-78E and the corresponding text in U.S. patent application Ser. No. 14/956,084, filed Dec. 1, 2015, titled "Intervertebral Implants and Related Systems and Methods," which has been incorporated herein by reference. Further, various arrangements of interbody devices 240 may include one or more features configured to facilitate sagittal and/or coronal visibility. For example, the body or frame 243 of interbody device 240 may comprise a radiopaque material visible via x-ray or similar forms of imaging modalities. As such, frame 243 may enable accurate positioning and/or placement of interbody device 240 within and/or along spinal column 2 (shown in FIG. 1). Frame 243 may include any one or more features such as anti-migration and/or anchoring features, anti-rotation features, insertion tool features, reduced profile keel features, and the like, as will be described in further detail below.

For instance, the frame 243 may include anti-migration and/or anchoring features 2432, 246. The features 2432 may be configured to contact and engage surface portions of, for example, a cage 102 (or 101) (shown in FIGS. 15A-15D) to secure the interbody device 240 to the cage 102. The features 2412 may be configured to assist in aligning and proper positioning of the interbody device 240 with respect to the cage 102 (or 101).

The anti-migration and/or anchoring features 246 may be located on upper and/or lower surfaces of the interbody device 240 that contact bone surface(s).

The features 2432 and/or 246 may comprise, for example, a pattern and/or texture that provides anti-migration and/or anchoring characteristics when implanted in the spine 1. The features 2432 and/or 246 may comprise, e.g., teeth, serrations, protrusions (e.g., triangular, pyramidal, conical, semi-spherical, rectangular, cylindrical, diamond, elliptical, and/or irregular shapes, or the like), or the like.

The frame 243 may include a channel 2433, as seen in FIGS. 13A and 13C. The channel 2433 may be provided on one or both inner walls of the frame 243. The channel 2433 may be configured to receive, engage and guide a plate guide of for example, a cage 102 (e.g., plate guide 146 of cage 102, shown in FIG. 4), thereby providing proper alignment and positioning of the interbody device 240 with respect to the cage 102 as seen in FIGS. 15A-15D).

Alternatively, the frame 243 may include a guide element (not shown), such as, for example, the plate guide 146 (shown in FIG. 4), that is configured to be received, engaged, and guided by a channel (not shown) that may be provided in the cage body.

The interbody device 240 may further include an engager element 2431. The engager element 2431 may be positioned and configured to align with and engage a plate engager, such as, for example, the plate engager 147 (shown in FIG. 4) to secure the interbody device 240 into final position with respect to the cage body (e.g., shown in FIGS. 15A-15C). The engager element 2431 may be arranged as a male element such as a protrusion, or the like, provided on an inner wall of the frame 243, or a female element such as a recess provided in the inner wall of the frame 243, or an opening formed through the wall of the frame 243, or the like. In this regard, the plate engager (e.g., plate engager 147, shown in FIG. 4) may include an oppositely configured element that engages and mates with the engager element 2431 to secure the cage (e.g., cage 102 shown in FIGS. 15A-15D) to the interbody device 240.

Retelling to FIGS. 13A-13C and 14 simultaneously, the interbody device 240 may be configured for use in, for example, anterior approach and disectomy applications. For instance, after a patient is positioned in a supine position on, for example, a radiolucent operating table, the surgical area cleaned, an incision made, muscle tissue and/or organs moved to the side(s) and other common surgical procedures carried out, a disc may be incised, removed, and the space prepared for implanting of an interbody device 240. The bone surfaces and edges on the adjacent vertebrae 4 may be carefully contoured, as appropriate.

Following a discectomy procedure, a medical professional may determine an appropriate size of the interbody device 240 by selecting an appropriately dimensioned interbody device 240, which may be selectable based on, for example, height, width, depth, surface angle(s), and the like. Upon selecting the appropriate interbody device 240, one or more of an ACIF, ALIF, or the like may be performed by placing the interbody device 240 between adjacent vertebrae 4 in the space formed by the removed degenerated disc (shown in FIG. 14). One or more fasteners 11 may be installed using an instrument (not shown), such as, for example, a screw driver (not shown). The locking element 247 may then be turned or otherwise manipulated to secure the fasteners 11 in place, thereby preventing the fasteners 11 from loosening or withdrawing from the bone.

Placement of the interbody device 240 within spinal column may prevent spaces between adjacent vertebrae 4 from collapsing, thereby preventing adjacent vertebrae from resting immediately on top of one another and inducing fracture of vertebra 4, impingement of the spinal cord, and/or pain. Additionally, such interbody device 240 may facilitate fusion (e.g., bone to grow together) between adjacent vertebrae 4 by stabilizing adjacent vertebrae 4 relative to one another.

FIGS. 15A-15E illustrate different views of an interbody system 300 that includes the interbody device 240 and the cage 102 (or 101, shown in FIGS. 3 and 4). The interbody system 300 may be formed as a single structure (not shown), or it may be assembled from two or more pieces.

For instance, referring to FIG. 15E, the interbody system 300 may be assembled by attaching, the interbody device 240 to the cage 102 (or 101). In this regard, interbody 240 may be positioned so that the channels 2433 are aligned with corresponding plate guides 146 on the cage 102, as seen in FIG. 15E. The interbody device 240 and cage 102 may then be move toward each other, with the plate guides 146 being received and guided by the respective channels 2433 as the cage 102 moves toward the back face 248 (shown in FIG. 13C) of the interbody device 240, until, for example, the engager element 2431 is aligned with and/or engages the plate engager 147, thereby securing the device 240 to the cage 102, to form the interbody system 300.

Figure 16C:
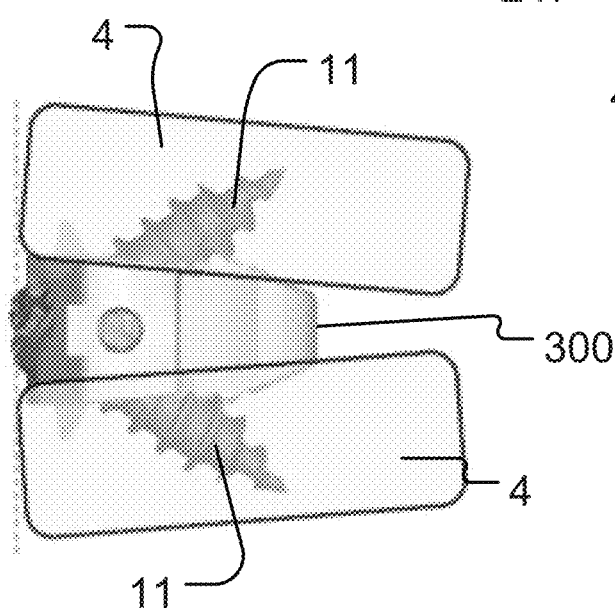

FIGS. 16A-16C illustrate an example of implanting the interbody system 300 between adjacent vertebrae 4. More specifically, FIG. 16A illustrates a top or superior (or bottom or inferior) cross-sectional view of the spine 2 (shown in FIG. 1) with the interbody system 300 implanted; FIG. 16B shows a perspective anterior coronal view of the implanted interbody system 300; and FIG. 16C shows a sagittal view of the implanted system 300.

The interbody system 300 may be configured for use in, for example, anterior approach and disectomy applications. The interbody system 300 may be implanted between the vertebrae 4 in similar manner to that described above with reference to FIG. 14. That is, the patient may be positioned in a supine position on, for example, a radiolucent operating table, the surgical area cleaned, an incision made, muscle tissue and/or organs moved to the side(s), and other common surgical procedures carried out. A disc may then be incised, removed, and the space prepared for implanting of the interbody system 300. The bone surfaces and edges on the adjacent vertebrae 4 may be carefully contoured, as appropriate.

Following the discectomy procedure, the medical professional may determine an appropriate size of the interbody system 300 by selecting an appropriately dimensioned interbody system 300, which may be selectable based on, for example, height, width, depth, surface angle(s), and the like. If the interbody device 240 and cage 102 are provided separately, the medical professional may select an interbody device 240 having appropriate dimensions (such as height, width, depth, surface angles, and the like) for the particular procedure and patient's anatomy, and the medical professional may similarly select a cage body 102 having appropriate dimensions (such as height, width, depth, surface angles, and the like) for the procedure and patient's anatomy. The medical professional may then assemble the interbody device 240 and cage 102 to form the interbody system 300, as shown in FIG. 15E. The medical professional may then place the interbody system 300 in the prepared space between the vertebrae 4.

Upon selecting the appropriate interbody system 300, one or more of an ACIF, ALIF, or the like may be performed by placing the interbody system 300 between adjacent vertebrae 4 in the space formed by the removed degenerated disc (shown in FIGS. 16B and 16C). One or more fasteners 11 may be installed using an instrument (not shown), such as, for example, a screw driver (not shown). As each fastener 11 is inserted through the aperture 242 and into contact with the wall membrane 162, the wall membrane 152 may bend and provide directional support against the skyping due to the springboard effect of wanting to back into its natural state, thereby urging the fastener 11 to the anchoring site. Simultaneously, due to the pushing of the wall membrane 162 into the graft chamber 150, the wall membrane may direct graft material from the graft chamber 150 to the areas surrounding the interbody system 300.

After the fasteners 11 are implanted in their final positions in the anchoring sites, the locking element 247 may be turned or otherwise manipulated to secure the fastener(s) 11 in place, thereby preventing the fastener(s) 11 from backing out (e.g., unscrewing) and/or dislodging from the anchor site(s).

Placement of the interbody system 300 within spinal column may prevent spaces between adjacent vertebrae 4 from collapsing, thereby prevent rig, adjacent vertebrae from resting immediately on top of one another and inducing fracture of vertebra 4, impingement of the spinal cord, and/or pain. Additionally, such interbody system 300 may facilitate fusion (e.g., bone to grow together) between adjacent vertebrae 4 by stabilizing adjacent vertebrae 4 relative to one another.

Figure 17A:
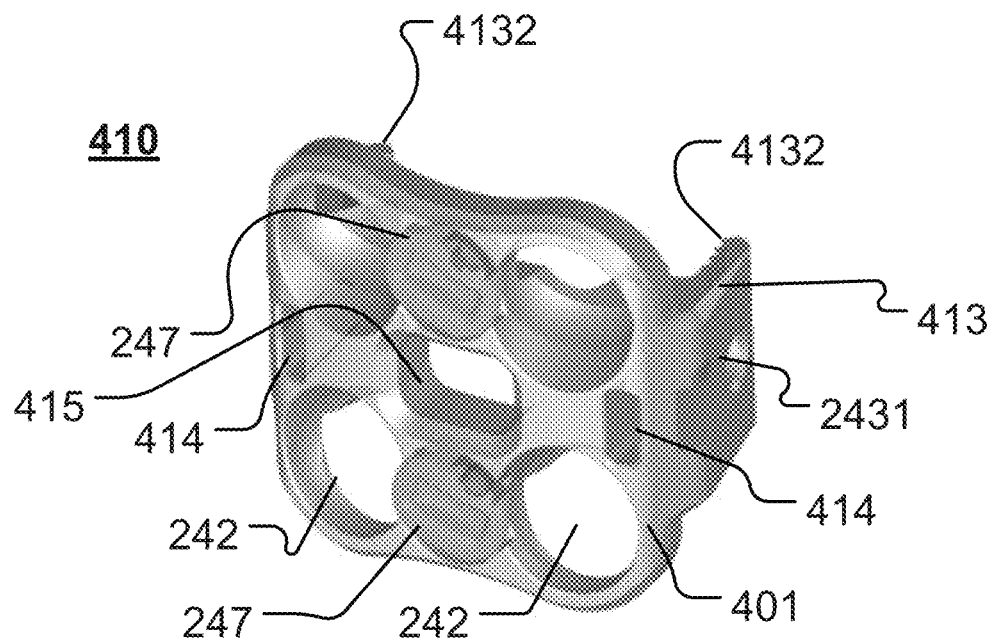
FIG. 17A illustrates a further example of an interbody device, constructed according to the principles of the disclosure.

FIG. 17A illustrates another example of an interbody device 410. The interbody device 410 may include the anterior coronal (or front) face 401 and a posterior coronal (or back face, not shown) defining a plurality (e.g., four) apertures 242 therebetween. The interbody device 410 may include one or more (e.g., two) locking elements 247.

The interbody device 410 may include a window 415. The window 415 may provide access and/or visibility to the space behind the back face (not shown) of the interface device 410. The window 415 may remain empty and/or may be filled with radiolucent material such as tissue grafts. The window 415 may enable a medical professional to view and/or determine the level of post-operative fusion between interbody device 410 and patient bone and/or tissue. The window 415 may be generally quadrilateral (e.g., square, rectangular, or trapezoidal). In some arrangements, a radiolucent structure, such as a graft containment sheath, may be disposed over the window. Indeed, such graft containment sheaths may substantially fill or encompass the window 244. Accordingly, when the interbody device 410 is placed between two adjacent vertebrae 4 under X-ray vision, window 415 remains radiolucent such that fusion within and/or through window 415 may be observed.

The interbody device 410 may include one or more (e.g., two) tool interfaces 414. The tool interfaces may be configured to be grasped by, attach to, or otherwise be contacted and engaged by a tool (not shown) during a medical implant procedure.

The interbody device 410 may be formed as a single piece (not shown), or it may be assembled from two or more pieces, such as, for example the frame 413 and a pair of the locking elements 247.

The body or frame 413 of the interbody device 410 may include anti-migration and, and/or anchoring features 4132. The features 4132 may be configured to contact and engage surface portions of, for example, the cage 102 (shown in FIGS. 17B-17E) to secure the interbody device 410 to the cage. The features 4132 may be configured to assist in aligning and proper positioning of the interbody device 410 with respect to the cage 102 in a manner similar to that described above with respect to the interbody device 240 and cage 102 (shown in FIG. 15E). The features 4132 may be configured similar to or substantially the same as the features 2432 described above.

The frame 413 may include anti-migration and/or anchoring features (not shown) located on upper and/or lower surfaces of the interbody device 410 to contact and engage adjacent bone surface(s). The features may comprise, for example, a pattern and/or texture that provides anti-migration and/or anchoring characteristics when implanted in the spine 2. The features may comprise, e.g., teeth, serrations, protrusions (e.g., triangular, pyramidal, conical semispherical, quadrilateral, rectangular cylindrical, diamond, elliptical, and/or irregular shapes, or the like), or the like.

The frame 413 may include a channel (not shown) similar to the channel 2433 shown in FIGS. 13A and 13C. The channel may be provided on one or both inner walls of the frame 413. The channel may be configured to receive, engage and guide the plate guide 146 of cage 102 (shown in FIG. 4) in a manner similar to or substantially the same as the channel 2432 described above, thereby providing proper alignment and positioning of the interbody device 410 with respect to the cage (e.g., shown in FIG. 17B).

As noted previously, the locking element 247 may be similar in construction and manner of use as described, for example, in FIGS. 3A-22D, 33, 35, 37, 39, 55, 58-65B, or 69A-78E and the corresponding text in U.S. patent application Ser. No. 14/956,084, filed Dec. 1, 2015, titled "Intervertebral implants and Related Systems and Methods," which has been incorporated herein by reference. Further, various arrangements of interbody device 410 may include one or more features configured to facilitate sagittal and/or coronal visibility. For example, the body or frame 413 of interbody device 410 may comprise a radiopaque material visible via x-ray or similar forms of imaging modalities. As such, frame 413 may enable accurate positioning and/or placement of interbody device 410 within and/or along spinal column 2 (shown in FIG. 1).

The Interbody device 410 may further include an engager element 2431 on at least one side of the frame 413, which may function in the manner described above with references to FIGS. 13A and 13B. The engager element 4131 may function in the same manner as the engager element 2431.

The interbody device 410 may be implanted in a manner similar to that described above for interbody device 240, with references to FIGS. 13A-13C and 14. The interbody device 410 may be configured for use in, for example, anterior approach and disectomy applications.

FIGS. 17B-17E illustrate various views of an example of an interbody system 400 that includes the interbody device 410. As seen, the interbody system 400 includes the interbody device 410 and the cage 102 (shown in FIG. 4). The interbody system 400 may be formed as a single structure (not shown), or it may be assembled from two or more pieces.

Figure 17B:
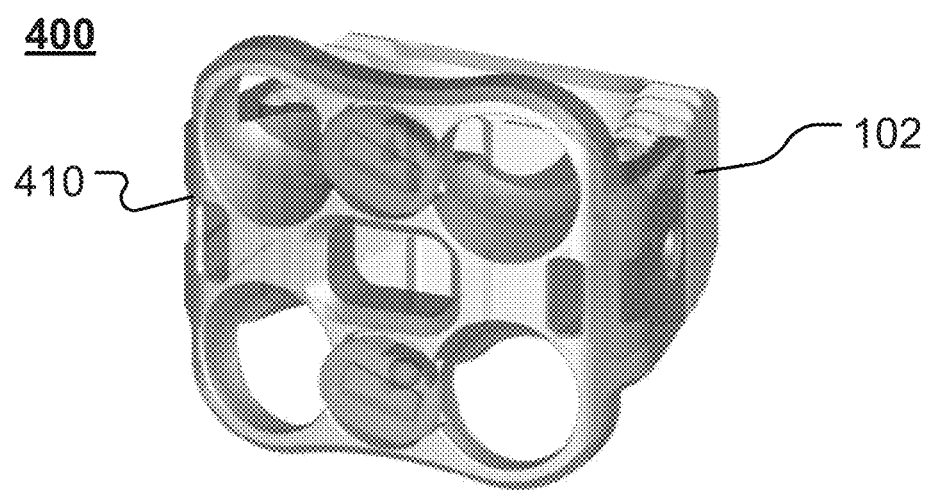
FIGS. 17B-17E illustrate various views of an example of an interbody system that includes the plate device of FIG. 17A.

For instance, referring to FIG. 17B, the interbody system 400 may be assembled by attaching the interbody device 410 to the cage 102 (or cage 101, shown in FIG. 3). In this regard, the interbody device 410 may be assembled in a manner similar to or substantially the same as that described above with references to FIG. 15E for the interbody system 300.

Figure 17C:
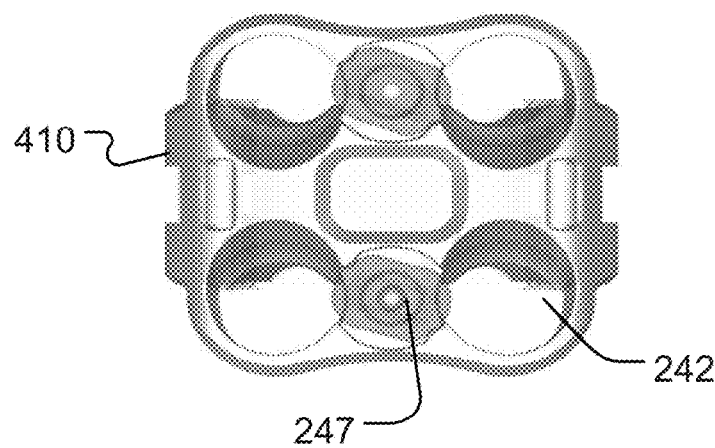

FIG. 17C an example of the interbody system 400 with the locking elements 247 positioned in a locking or near-locking position. As seen, a portion of the locking elements 247 is turned and positioned in the aperture(s) 242, thereby partially (or entirely) blocking the aperture(s) 242, so that the bone fastener 11 (shown in FIG. 18B) is prevented from backing out of the aperture 242.

Figure 17D:
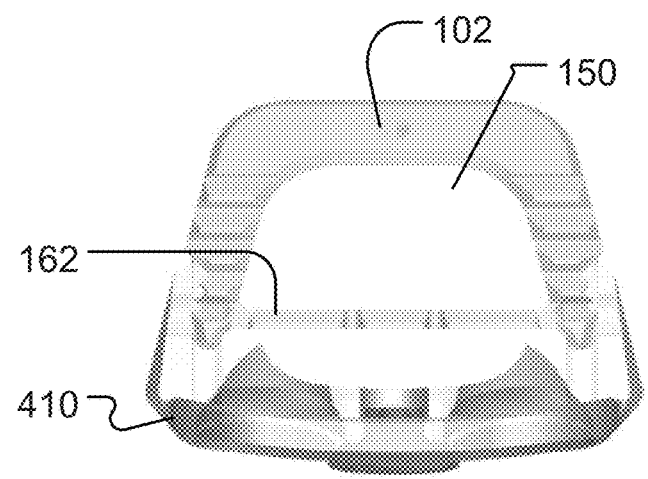

FIG. 17D shows a superior (or inferior) view of the interbody system 400.

Figure 17E:
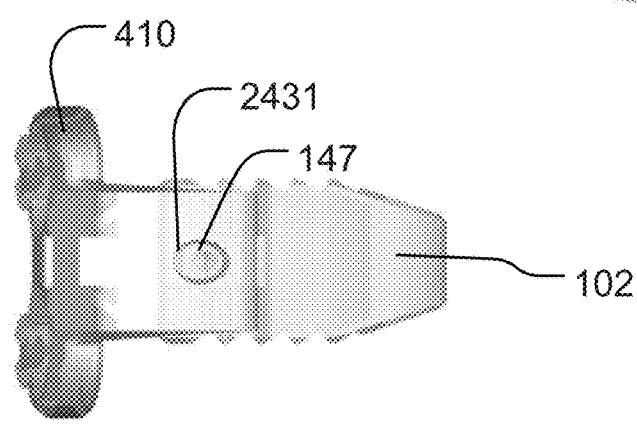

FIG. 17E shows a sagittal view of the interbody system 400.

Figure 18A:
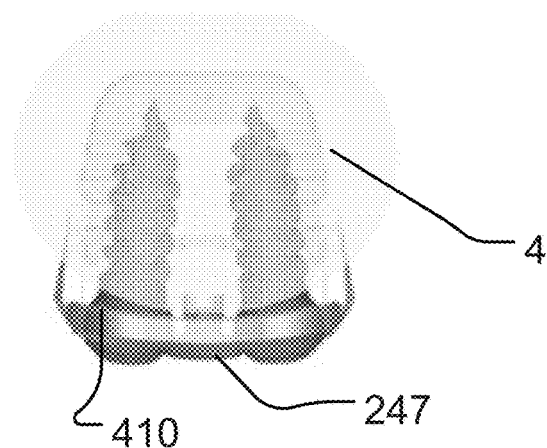
FIGS. 18A-18C illustrate an example of the interbody system of FIGS. 17B-17E installed between a pair of bony structures.
Figure 18B:
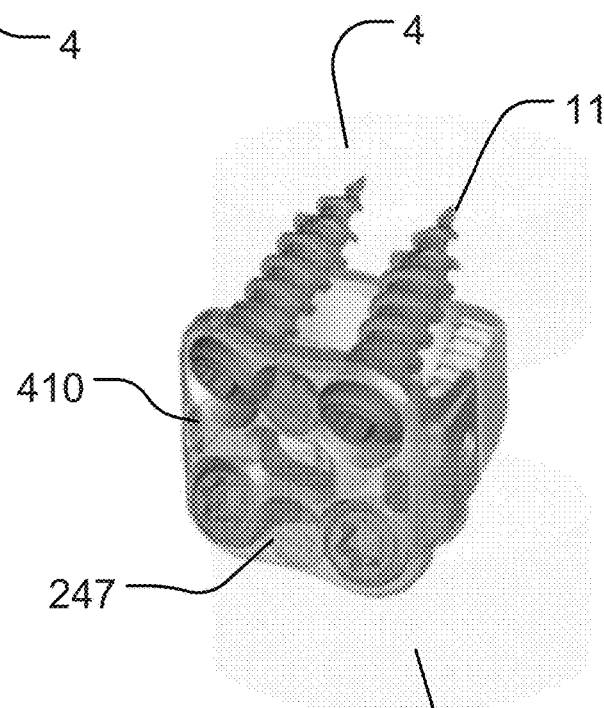
Figure 18C:
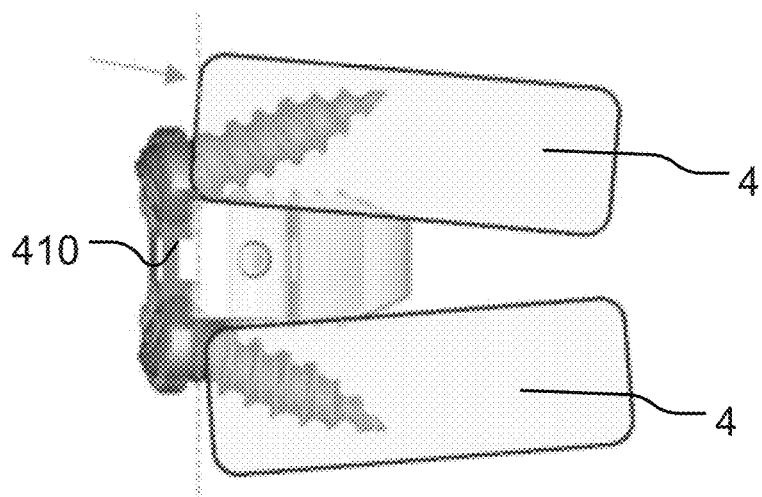

FIGS. 18A-18C illustrate an example of implanting the interbody system 400 between a pair of bony structures (e.g., vertebrae) 4.

Referring to FIGS. 17B-17E and 18A-18C simultaneously, the interbody system 400 may be configured for use in, for example, anterior approach and disectomy applications. For instance, after a patient is positioned in a supine position on, for example, radiolucent operating table, the surgical area cleaned, an incision made, muscle tissue and/or organs moved to the side(s), and other common surgical procedures carried out, a disc may be incised, removed, and the space prepared for implanting of an interbody system 400. The bone surfaces and edges on the adjacent vertebrae 4 may be carefully contoured, as appropriate.

Following a discectomy procedure, a medical professional may determine an appropriate size of the interbody device 410 and/or the cage 102 (or 101) by selecting an appropriately dimensioned interbody device 410 and/or an appropriately dimensioned cage 102 (or 101), each of which may be selectable based on, for example, height, width, depth, surface angle(s), and the like. Where the interbody system 400 is provided as a single unit, the interbody system 400 as a unit may be selected based on its dimensions for the particular application.

Upon selecting the appropriate interbody system 400 (e.g., interbody device 410 and cage 102), one or more of an ACIF, ALIF, or the like may be performed by placing the interbody system 400 between adjacent vertebrae 4 in the space formed by the removed degenerated disc (shown in FIGS. 18A-18C). The medical professional may then place the cage portion of the interbody system 400 in the space between the vertebrae 4. The medical professional may prepare the coronal surfaces of the adjacent vertebrae 4 by removing bone material to substantially match the outer perimeter of the interbody device 410, so as to receive at least a portion of the interbody device 410 in the prepared areas on the vertebrae 4 and thereby position the anterior coronal face 401 of the interbody device 410 (shown in FIG. 17A) substantially flush with the anterior coronal surfaces of the adjacent vertebrae 4.

Once the interbody system 400 is seated in its final position, four bone fasteners 11 may be installed using an instrument (not shown), such as, for example, a screw driver (not shown). As each fastener 11 is inserted through the aperture 242 and into contact with the wall membrane 162, the wall membrane 162 may bend and provide directional support against the skyping due to the springboard effect of wanting to back into its natural state. Simultaneously, due to the pushing of the wall membrane 162 into the graft chamber 150, the wall membrane may direct graft mater al from the graft chamber 150 to the areas surrounding the interbody system 400.

After the fasteners 11 are implanted in their final positions in the anchoring sites, the locking element 247 may then be turned or otherwise manipulated to secure the fasteners 11 in place, thereby preventing the fasteners 11 from loosening or withdrawing from their respective anchoring sites.

After the bone graft materials are installed, and the bone fasteners 11 are securely and properly placed, and the installation of the interbody system 400 (or 300) completed, the area may be cleaned, checked, closed and other postoperative procedures carried out, as is known in the art.

Placement of the interbody system 400 within spinal column may prevent spaces between adjacent vertebrae 4 from collapsing, thereby preventing adjacent vertebrae from resting immediately on top of one another and inducing fracture of vertebra 4, impingement of the spinal cord, and/or pain. Additionally, such in system 400 may facilitate fusion (e.g., bone to grow together) between adjacent vertebrae 4 by stabilizing adjacent vertebrae 4 relative to one another.

In the instant disclosure, where the fastener 11 includes a bone screw, a thread may be tapped into the bone to form a tap (not shown) to receive and securely hold the bone fastener 11. The process would be repeated for each fastener 11. Such holes may be formed with the aid of a separate drill guide (not shown) positioned proximate or abutting vertebra 4 and inserting a drill therethrough. Alternatively, such holes may be formed free band, without the use of a drill guide.

After the interbody device or interbody system is properly installed with respect to the vertebrae 4 (e.g., a shown in FIG. 14, 16A-16C or 18A-18C), the bone fasteners) 11 may be installed. In this regard, a driver tool (not shown), as is known by those skilled in the art, may be used to turn and drive the bone fastener(s) 11 into the vertebrae 4. It is noted that the bone fastener(s) 11 may be aligned with the tap (not shown) in the bone and screwed into the threaded tap. Alternatively, the bone fasteners 11 may be partially installed in the tap before bent contacted by the driver tool. Once the bone fasteners 11 are implanted in the desired position, the driver tool may be removed and the process repeated for each bone fastener 11.

The terms "including," "comprising," and variations thereof, as used in this disclosure, mean "including, but not limited to," unless expressly specified otherwise.

The terms "a," "an," and "the," as used in this disclosure, means "one or more," unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, or the like, may be described in a sequential order, such processes and methods may be configured to work in alternate orders. In other words, any sequence or order of steps that may be described does not necessarily indicate a requirement that the steps be performed in that order. The steps of the processes or methods described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

While the disclosure has been described in terms of exemplary embodiments, those skilled in the art will recognize that the disclosure can be practiced with modifications in the spirit and scope of the appended claims. These examples are merely illustrative and are not meant to be an exhaustive list of all possible designs, embodiments, applications or modifications of the disclosure.

The invention claimed is:

1. An interbody system for implanting between vertebrae, comprising
a cage body that includes a pair of sagittal walls, an aft-wall and a wall membrane that is made of a shape memory form material, and
an interbody device that attaches to the cage body, wherein the interbody device comprises an aperture that receives a bone fastener, and wherein the wall membrane bends under a force applied by the bone fastener.

2. An interbody system for implanting between vertebrae, comprising:
a cage having a cage body that includes
a graft chamber having a volume that receives graft material,
a sagittal wall that forms a portion of the graft chamber, and
a wall membrane that forms another portion of the graft chamber, wherein the wall membrane interacts with a bone fastener.

3. The interbody system of claim 2, wherein the wall membrane interacts with the bone fastener to bend as result of a force applied by the bone fastener to a portion of the wall membrane, thereby providing directional support to the bone fastener.

4. The interbody system of claim 2, wherein the wall membrane interacts with the bone fastener to bend as result of a force applied by the bone fastener to reduce the volume of the graft chamber, thereby forcing graft material from the graft chamber.

5. The interbody system of claim 2, the system further comprising: an interbody device that includes an aperture that receives the bone fastener, wherein the wall membrane comprises a slit.

6. The interbody system of claim 5, wherein the slit facilitates bending of a portion of the wall membrane as a result of a force applied to said portion of the wall membrane.

7. An interbody system for implanting between vertebrae, comprising:
a cage having a cage body that includes
a graft chamber having a volume that receives graft material,
a first sagittal wall having an inner wall surface that forms a first sagittal portion of the graft chamber,
a second sagittal wall having an inner wall surface that forms a second sagittal portion of the graft chamber,
an aft-wall having an inner wall surface that forms a posterior coronal portion of the graft chamber, and
a wall membrane that forms an anterior coronal portion of the graft chamber; and
an interbody device that includes an aperture that receives a bone fastener,
wherein the wall membrane is directly adjacent to the bone fastener.

8. The interbody system of claim 7, wherein the wall membrane contacts the bone fastener to provide directional support to the bone fastener.

9. The interbody system of claim 7, wherein the wall membrane contacts the bone fastener and bends as result of a force applied by the bone fastener to thereby reduce the volume of the graft chamber.

10. The interbody system of claim 7, wherein the wall membrane comprises a slit.

11. The interbody system of claim 10, wherein the slit facilitates bending of a portion of the wall membrane as a result of a force applied to said portion of the wall membrane.

12. The interbody system of claim 10, wherein the slit receives and guides the bone fastener.

13. The interbody system of claim 7, wherein the wall membrane comprises:
a thin sheet that is integrated with or attached to the cage body;

a thin mesh that is integrated with or attached to the cage body;

a thin screen that is integrated with or attached to the cage body; or a beams screen that is integrated with or attached to the cage body.

14. The interbody system of claim 7, wherein the sagittal wall comprises a recessed wall portion located proximate to the wall membrane.

15. The interbody system of claim 7, wherein the graft chamber comprises:

a first chamber width portion that holds graft material; and a second chamber width portion that holds graft material, wherein the width of the first chamber width portion is greater than the width of the second chamber width portion.

16. The interbody system of claim 7, wherein the sagittal wall comprises a grip interface that contacts and engages a grip interface provided on the interbody device to secure the cage to the interbody device.

17. The interbody system of claim 7, wherein the interbody device comprises two or more apertures that receive two or more respective bone screws.

18. The interbody system of claim 7, wherein the cage body comprises a plate guide that engages a cage guide provided on the interbody device to facilitate proper positioning and alignment of the cage with respect to the interbody device.

19. The interbody system of claim 7, wherein the cage body comprises a plate engager that aligns with a cage engager provided on the interbody device to secure the cage body to the interbody device.

* * * * *